(12) United States Patent
Groenewegen et al.

(10) Patent No.: US 8,900,615 B2
(45) Date of Patent: *Dec. 2, 2014

(54) DRUG DELIVERY SYSTEM

(71) Applicant: Merck Sharp & Dohme B.V., Oss (NL)

(72) Inventors: Rudolf Johannes Joseph Groenewegen, Oss (NL); Wouter de Graaff, Oss (NL)

(73) Assignee: Merck Sharp & Dohme B.V., Haarlem (NL)

( * ) Notice: Subject to any disclaimer, the term of this patent is extended or adjusted under 35 U.S.C. 154(b) by 222 days.

This patent is subject to a terminal disclaimer.

(21) Appl. No.: 13/672,804

(22) Filed: Nov. 9, 2012

(65) Prior Publication Data

US 2013/0115265 A1 May 9, 2013

Related U.S. Application Data

(63) Continuation of application No. 10/558,040, filed as application No. PCT/EP2004/000850 on May 19, 2004, now Pat. No. 8,333,983.

(60) Provisional application No. 60/473,055, filed on May 23, 2003.

(30) Foreign Application Priority Data

May 23, 2003 (EP) ..................... 03101490

(51) Int. Cl.
| | | |
|---|---|---|
| *A61F 2/00* | (2006.01) | |
| *A61F 6/06* | (2006.01) | |
| *A61F 13/00* | (2006.01) | |
| *A61F 13/02* | (2006.01) | |
| *A61K 45/06* | (2006.01) | |
| *A61K 9/00* | (2006.01) | |
| *A61K 31/57* | (2006.01) | |
| *A61K 9/24* | (2006.01) | |
| *A61K 31/565* | (2006.01) | |
| *A61K 31/567* | (2006.01) | |

(52) U.S. Cl.
CPC ............... *A61K 9/0036* (2013.01); *A61K 45/06* (2013.01); *A61K 9/0092* (2013.01); *A61K 31/57* (2013.01); *A61K 9/00* (2013.01); *A61K 9/209* (2013.01); *A61K 31/565* (2013.01); *A61K 31/567* (2013.01)
USPC ............ 424/422; 424/430; 424/432; 424/433

(58) Field of Classification Search
None
See application file for complete search history.

(56) References Cited

U.S. PATENT DOCUMENTS

| | | | |
|---|---|---|---|
| 3,854,480 | A | 12/1974 | Zaffaroni |
| 3,995,633 | A | 12/1976 | Gougeon |
| 3,995,634 | A | 12/1976 | Drobish |
| 4,237,885 | A | 12/1980 | Wong et al. |
| 4,292,965 | A | 10/1981 | Nash et al. |
| 4,596,576 | A | 6/1986 | de Nijs |
| 4,666,702 | A | 5/1987 | Junginger |
| 5,972,372 | A | 10/1999 | Saleh et al. |

FOREIGN PATENT DOCUMENTS

| | | |
|---|---|---|
| EP | 0 050 867 B1 | 1/1988 |
| EP | 0 303 306 B1 | 3/1993 |
| EP | 0 876 815 B1 | 1/2001 |
| ES | 2 166 894 T3 | 5/2002 |
| WO | 97/02015 A1 | 1/1997 |
| WO | 99/30976 A1 | 6/1999 |

OTHER PUBLICATIONS

Davies, G. C. et al., "The effects of a combined contraceptive vaginal ring releasing ethinyloestradiol and 3-Ketodesogestrel on vaginal flora", Contraception, 1992, p. 511-518, vol. 45.

Kubba, A. et al., "Contraception", The Lancet, 2000, p. 1913-1919, vol. 356.

Van Laarhoven, J. A. H. et al., "Effect of supersaturation and crystallization phenomena on the release properties of a controlled release device based on EVA copolymer", Journal of Controlled Release, 2002, p. 309-317, vol. 82.

Van Laarhoven, J. A. H. et al., "In vitro release properties of etonogestrel and ethinyl estradiol from a contraceptive vaginal ring", International Journal of Pharmaceutics, 2002, p. 163-173, vol. 232.

*Primary Examiner* — Robert A Wax
*Assistant Examiner* — Caralynne Helm
(74) *Attorney, Agent, or Firm* — Janet E. Fair; Catherine D. Fitch

(57) ABSTRACT

The subject invention provides a drug delivery system comprising at least one compartment consisting of (i) a drug-loaded thermoplastic polymer core, (ii) a drug-loaded thermoplastic polymer intermediate layer and (iii) a non-medicated thermoplastic polymer skin covering the intermediate layer, wherein said intermediate layer is loaded with (a) crystals of a first pharmaceutically active compound and with (b) a second pharmaceutically active compound in dissolved form and wherein said core is loaded with said second compound in dissolved form.

6 Claims, 21 Drawing Sheets

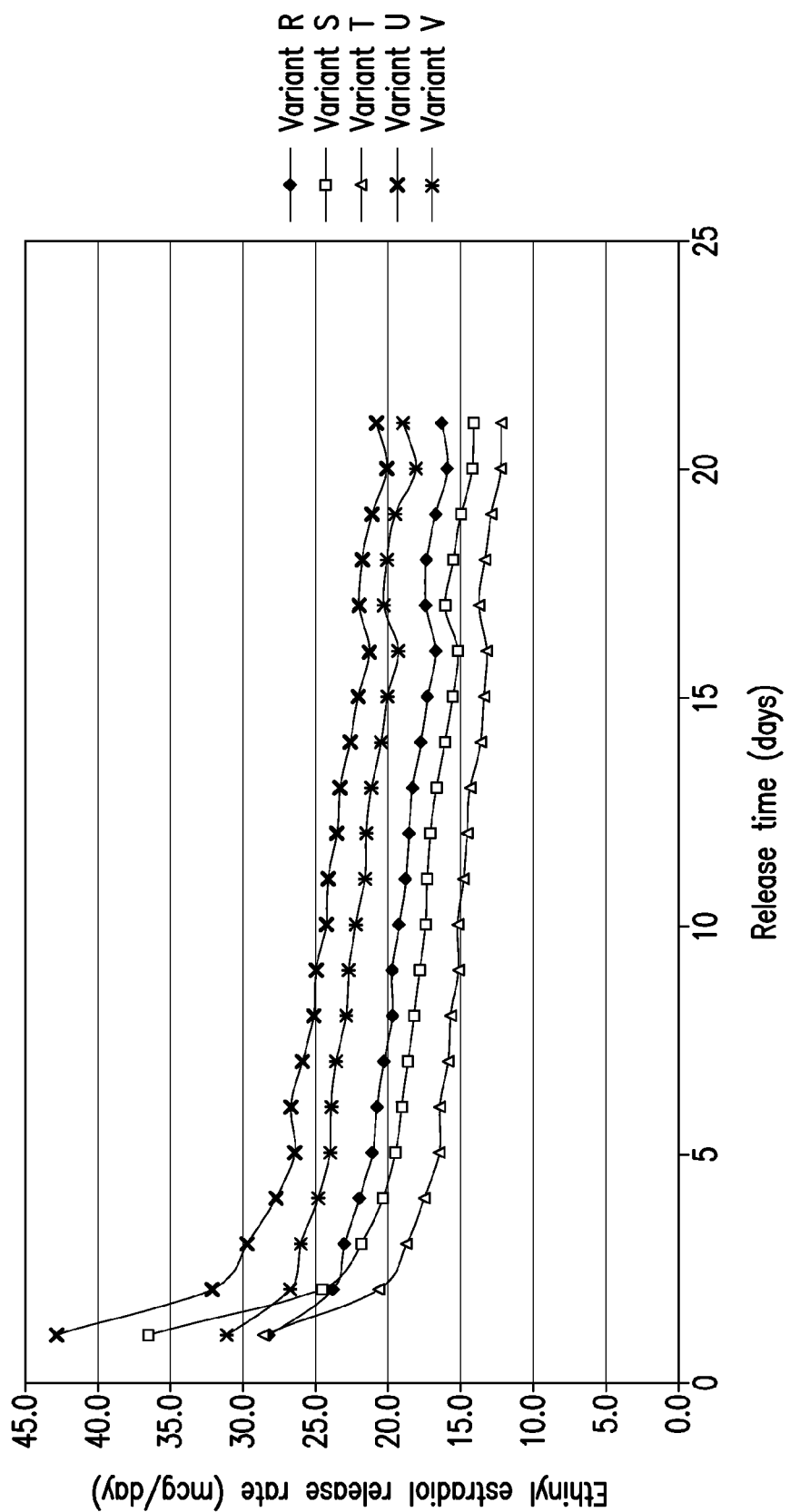

DRUG DELIVERY SYSTEM

CROSS-REFERENCE TO RELATED APPLICATIONS

Figure 1:
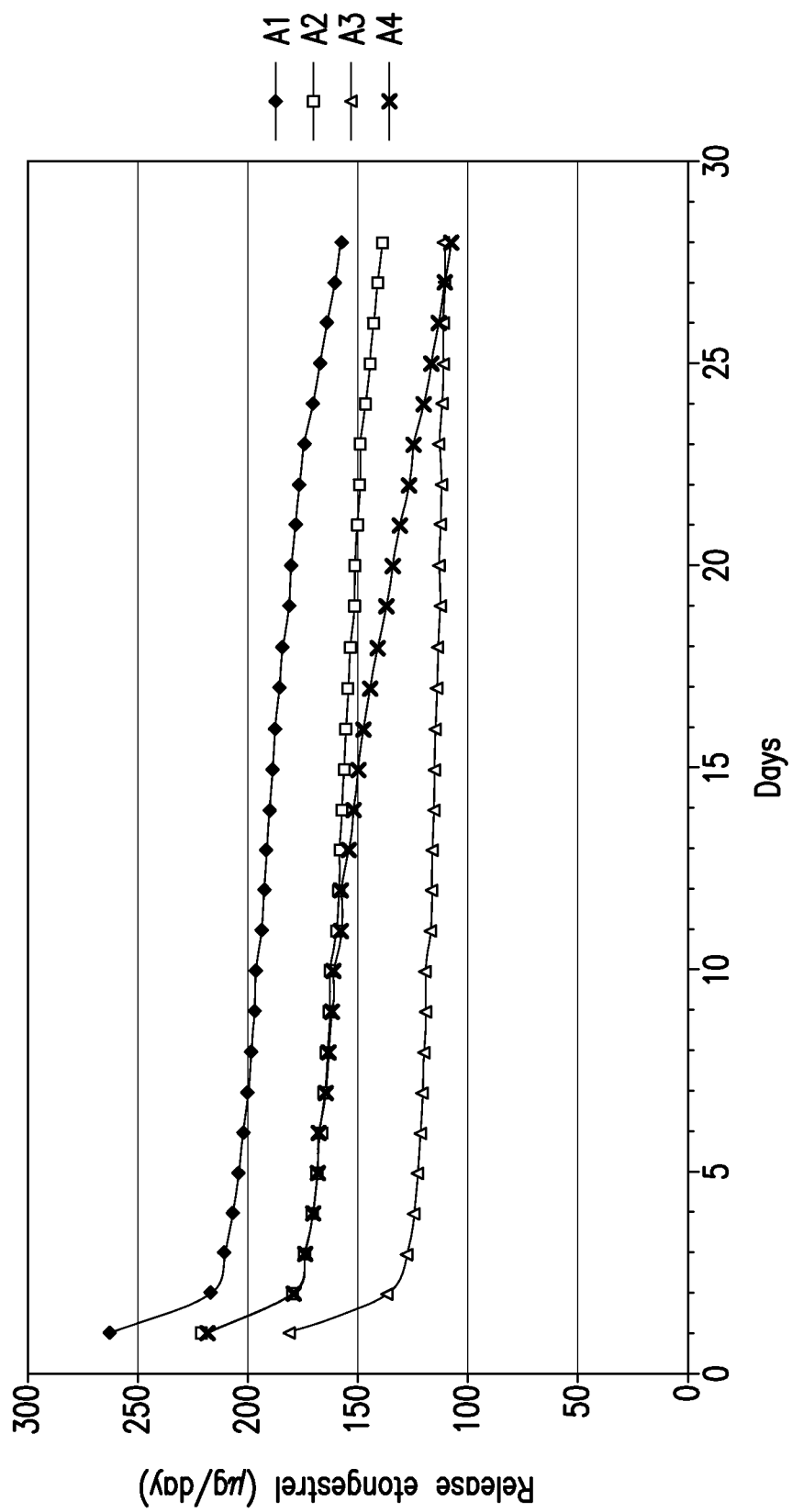

This application is a continuation of U.S. application Ser. No. 10/558,040 which is a U.S. National Phase application under 35 U.S.C. §371 of PCT Application No. PCT/EP2004/00850, filed May 19, 2004, which published as WO 2004/10336A1 on Dec. 2, 2004 and claims priority under 35 U.S.C. §365(b) from U.S. provisional patent application No. 60/473,055, filed May 23, 2003 and European patent application No. 03101490.5.

FIELD OF THE INVENTION

The present invention relates to the field of female contraception and hormone replacement therapy.

The present invention relates to a drug delivery system (device) for the simultaneous release of two or more active substances and more particularly to a ring shaped vaginal drug delivery system, which system releases the active substances in a substantially constant ratio over a prolonged period of time. Since the invention pertains to a drug delivery article for intra-vaginal use, its use is focussed on typically female medical indications, such as contraception and hormone-replacement. The article according to the invention is particularly in the form of a ring, and will hereinafter be referred to as a vaginal ring.

BACKGROUND OF THE INVENTION

Vaginal rings are known. Background art in this respect includes the following patent documents.

U.S. Pat. Nos. 3,995,633 and 3,995,634, describe separate, preferably spherical or cylindrical, reservoirs containing different active substances which are assembled in specially constructed holders.

U.S. Pat. No. 4,237,885 describes a tube or coil of polymeric material which is divided into portions by means of a plurality of "spacers" provided in the tube, after which each of the separate tube portions is filled with a different active substance in a silicone fluid and the two ends of the tube are subsequently connected to one another. In this release system, however, transport (diffusion) of active material from one reservoir to the other takes place through the wall of the tube, especially upon prolonged storage, so that the pre-set fixed release ratio between the active substances in question will change over a period of time.

European patent publication 0,050,867 discloses a two-layered vaginal ring which comprises a pharmacologically acceptable supporting ring covered by two layers preferably of silicone elastomers whereby the inner layer is a silicone elastomer loaded with an active substance.

U.S. Pat. No. 4,292,965 describes a ring shaped vaginal delivery system of three layers made of silicone elastomers.

U.S. Pat. No. 4,596,576 describes a two-compartment vaginal ring wherein each compartment contains a different active substance. To achieve a suitable ring with a constant release ratio between the various active substances, the end portions of the compartments are joined by glass stoppers.

Patent Publication WO 97/02015 describes a two-compartments device, a first compartment consisting of a core, a medicated middle layer and a non medicated outer layer, and a second compartment consisting of a medicated core and a non medicated outer layer.

EP 876 815 discloses a vaginal ring (Nuvaring®) which is designed for the simultaneous release of a progestogenic steroid compound and an estrogenic steroid compound in a fixed physiological ratio over a prolonged period of time. The drug delivery system comprises one compartment comprising a thermoplastic polymer core containing the mixture of the progestogenic and estrogenic compounds and a thermoplastic polymer skin, the progestogenic compound being initially dissolved in the polymer core material in a relatively low degree of supersaturation.

From the above disclosures, it is clear that e.g. the material, the layers and the compartments are all aspects of a ring device which play a role in the designs that have been developed.

All choices are usually made with a view to obtain a constant release pattern, which is complicated when two or more active substances are involved. The latter is of particular importance in the field of contraception, as for this purpose often a combination of a progestagen and an estrogen is used. Also in hormone replacement, however, it is desired to have rings which deliver combinations of drugs.

Among the above disclosures, EP 876 815 clearly sets a standard; it involves a one-compartment design, it obviates the need for silastic polymer by using EVA combinations, and it releases two or more active substances in a substantially constant ratio to one another over a prolonged period in time.

As any product of technology at all times however, also the latter can still be improved upon. The drug delivery device disclosed in EP 876815 is physically stable only when stored below room temperature. It requires storage and transport below room temperature which is expensive and requires a lot of attention. Moreover, if not stored below room temperature, steroid eventually crystallizes out onto the skin of the device which may lead to uncontrollable and high burst release.

The subject improved drug delivery system solves this problem since it is physically stable under room temperature conditions and thus does not need special storage and transportation conditions.

Moreover, in the subject improved drug delivery system, it is possible to adjust the release rate of more than one pharmaceutically active compound independently from one another, while maintaining the physical stability of the system.

SUMMARY OF THE INVENTION

The subject invention provides a three-layer design vaginal ring, physically stable at room temperature, from which at least two pharmaceutically active compounds can be released independently from one another.

The ring comprises at least one compartment comprising (i) a medicated thermoplastic polymer core, (ii) a medicated thermoplastic polymer intermediate layer and (iii) a non-medicated thermoplastic polymer skin covering the intermediate layer. The intermediate layer is medicated (loaded) with (a) crystals of a first active substance and with (b) a second active substance in dissolved form. The core is loaded with the second active substance as well, optionally in the same concentration as in the intermediate layer.

FIGURES

Figure 2:
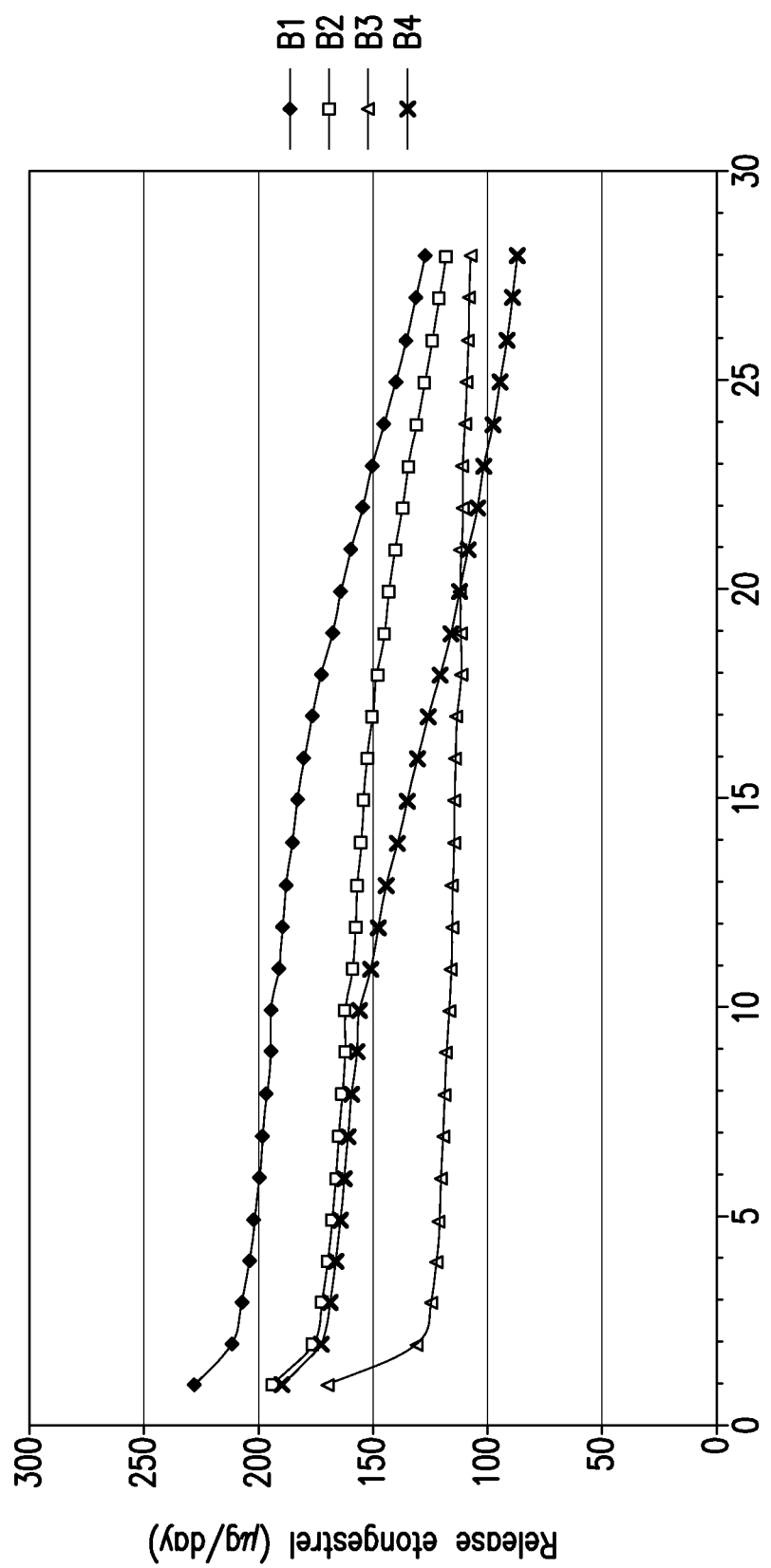

FIG. 1:
In vitro release rates of etonogestrel (ENG) for all 4.0 mm batches.
FIG. 2:
In vitro release rates of etonogestrel for all 3.5 mm batches.

Figure 3:
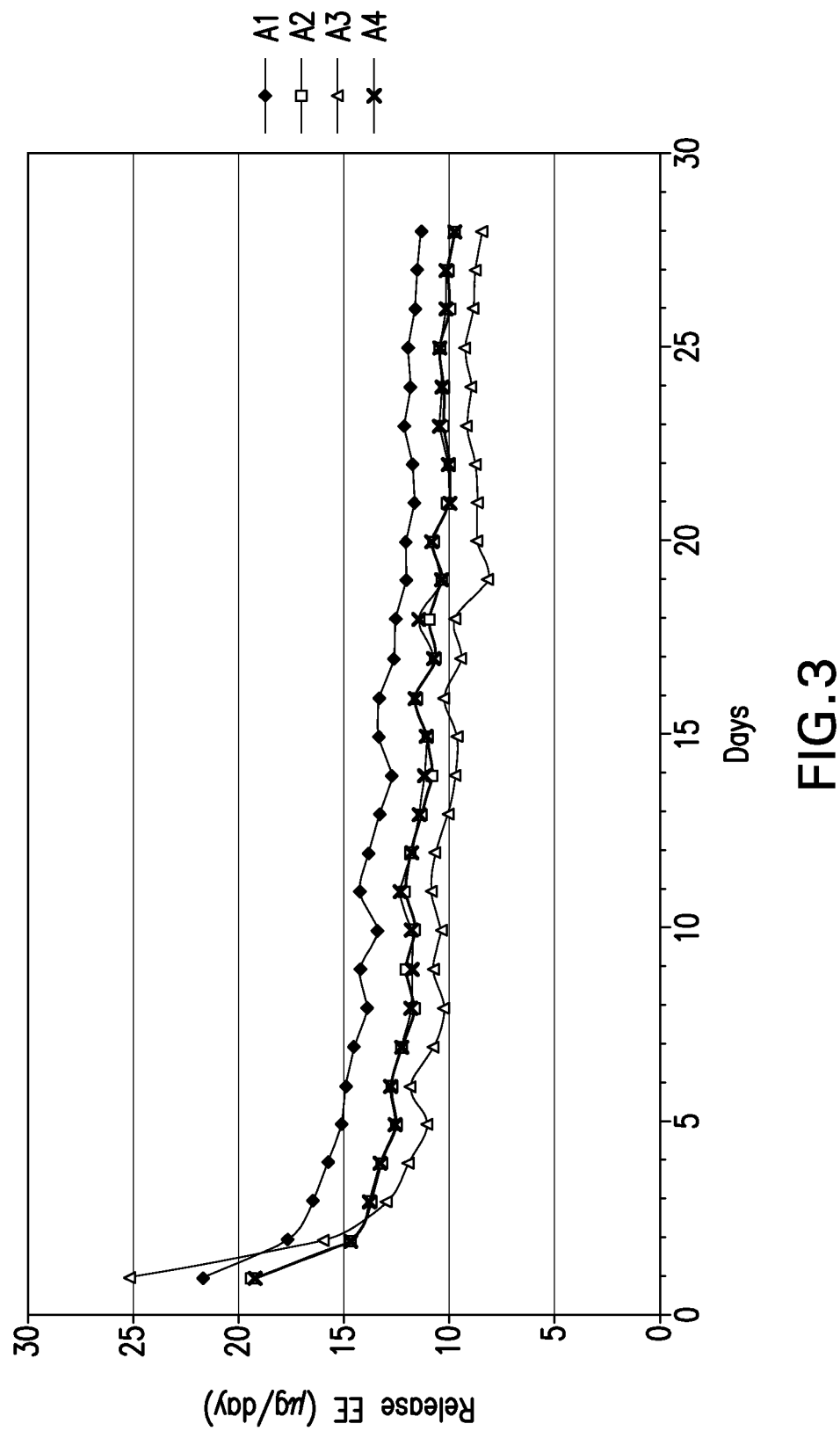
Figure 4:
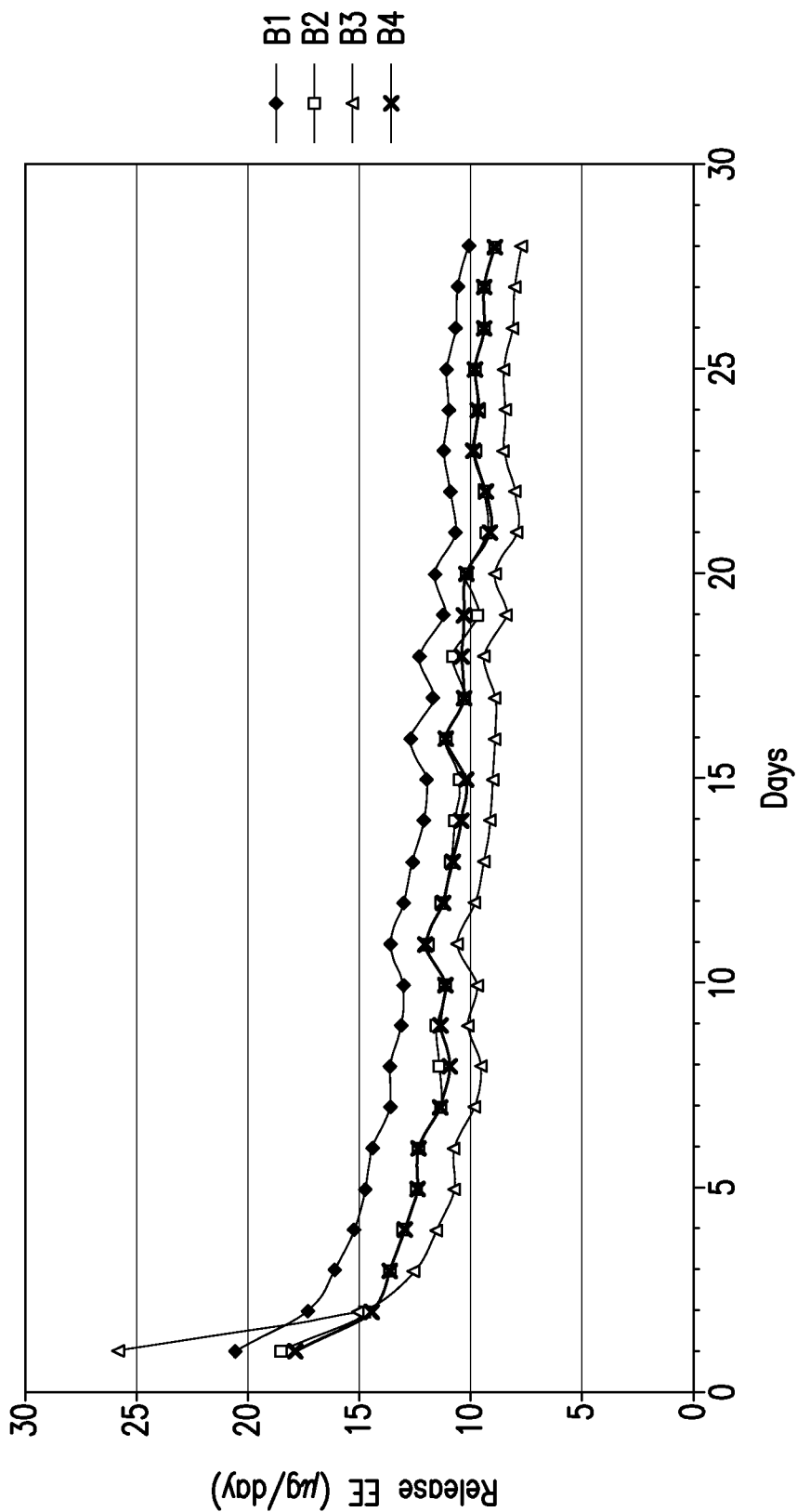
Figure 5:
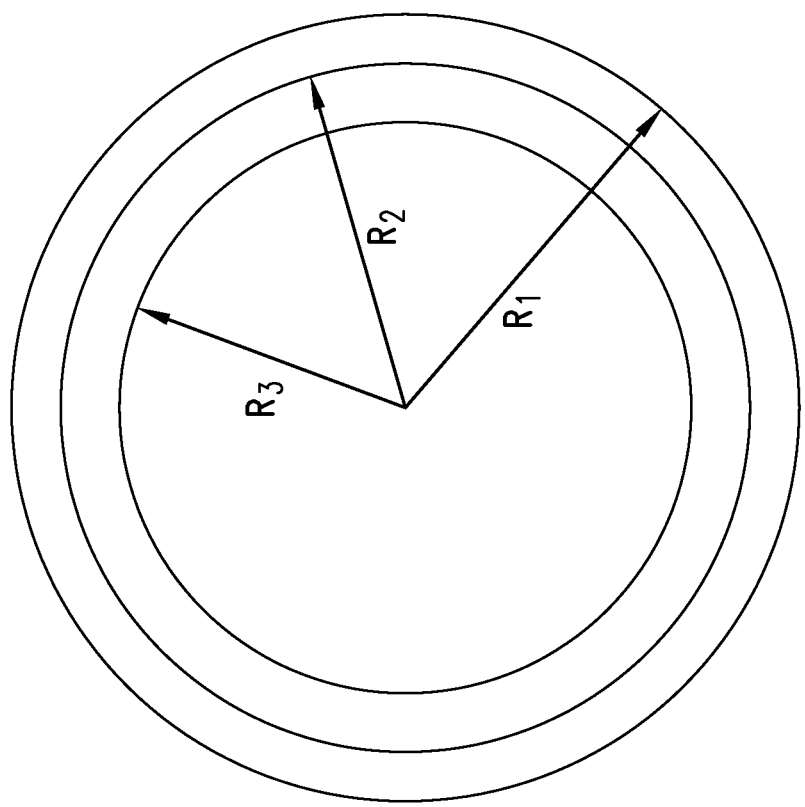
Figure 6:
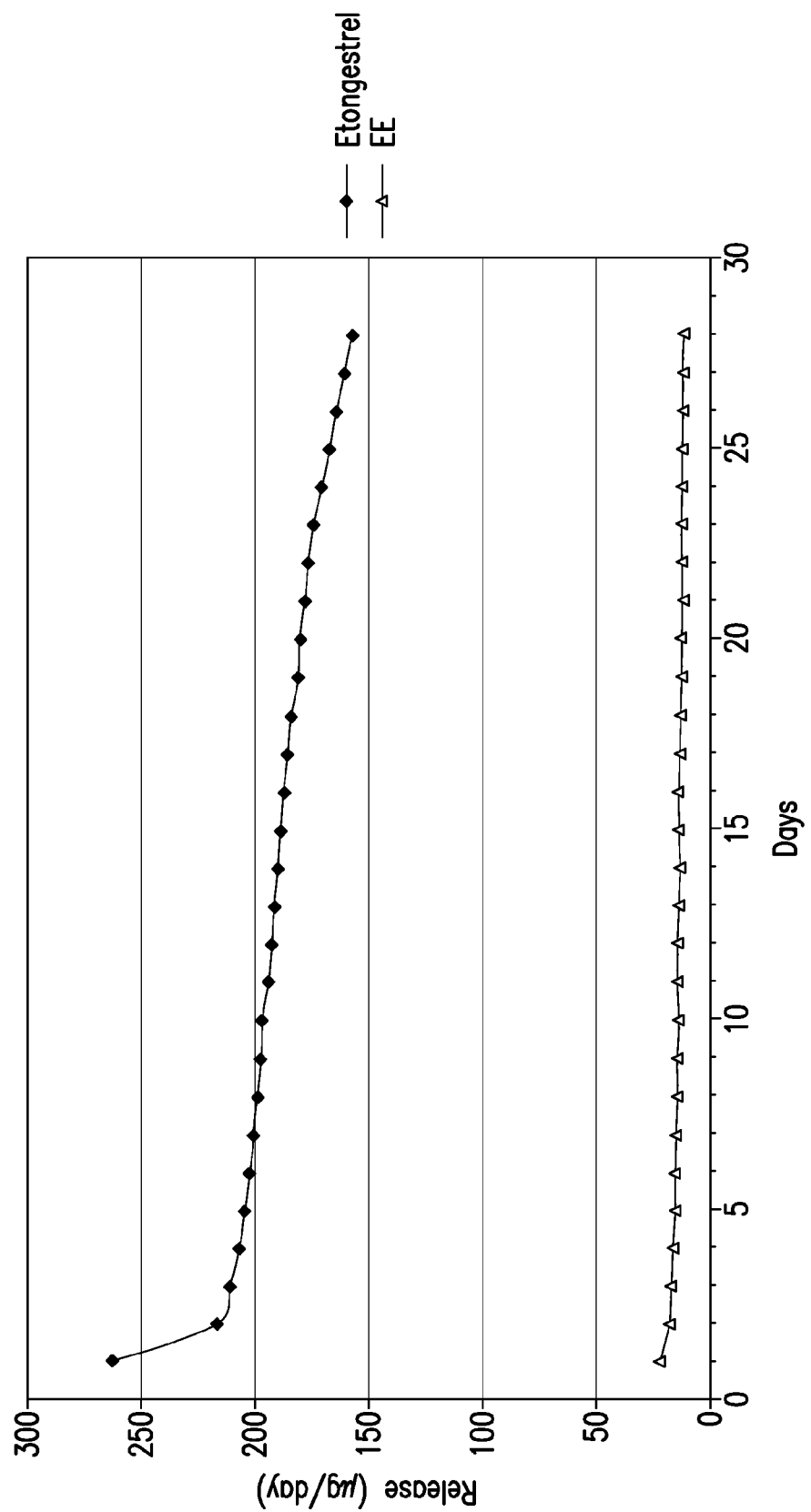
Figure 7:
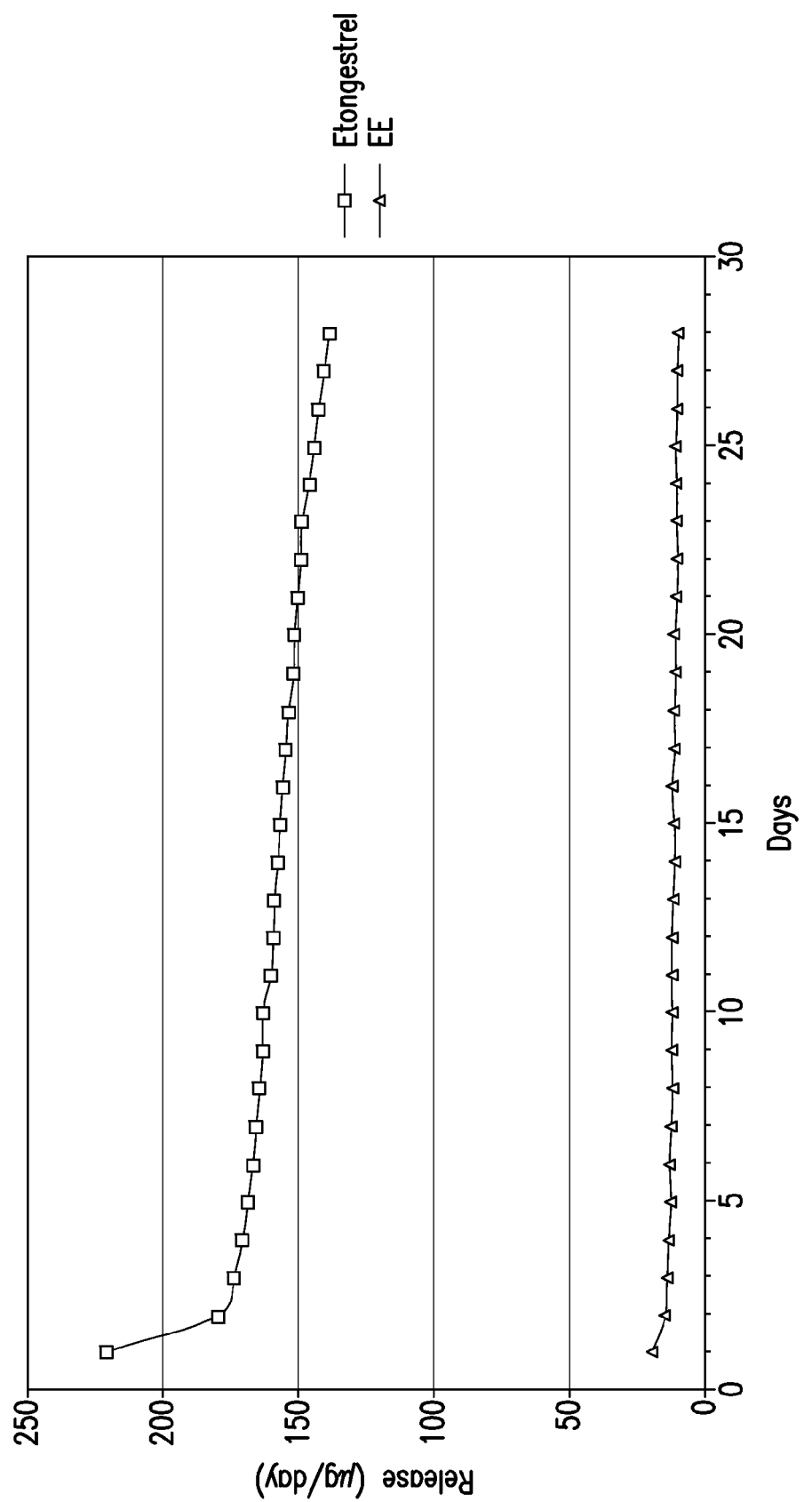
Figure 8:
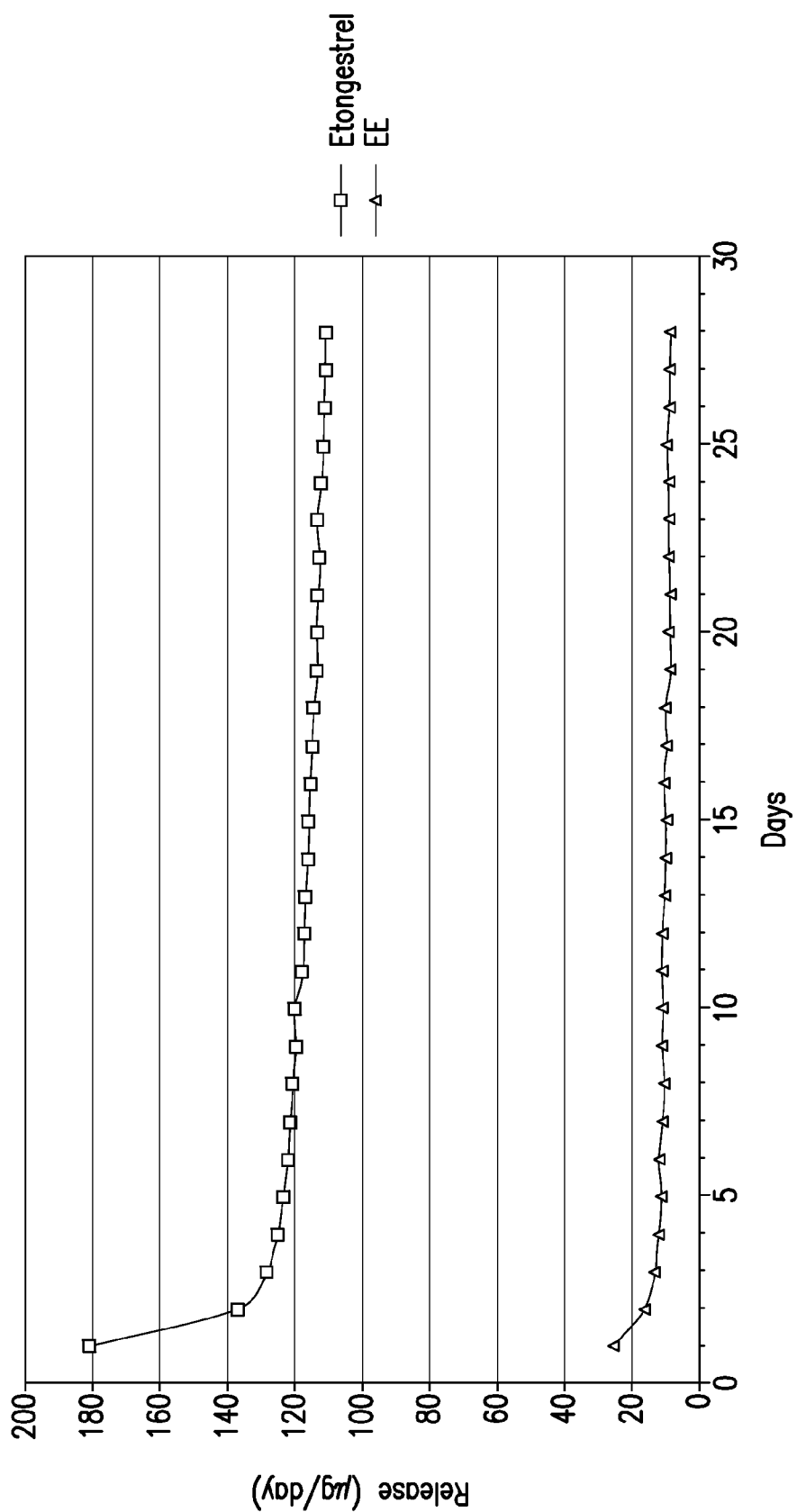
Figure 9:
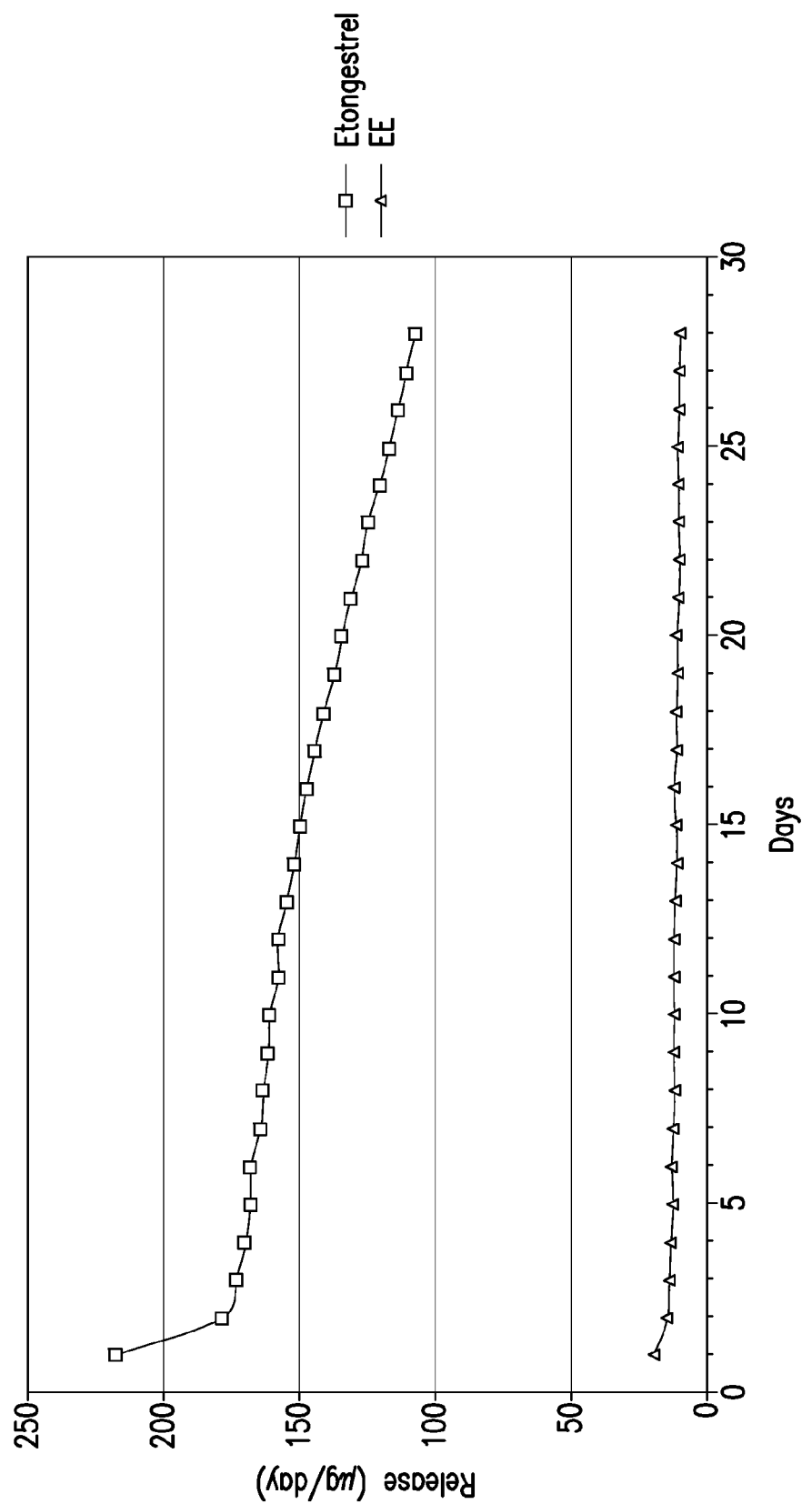
Figure 10:
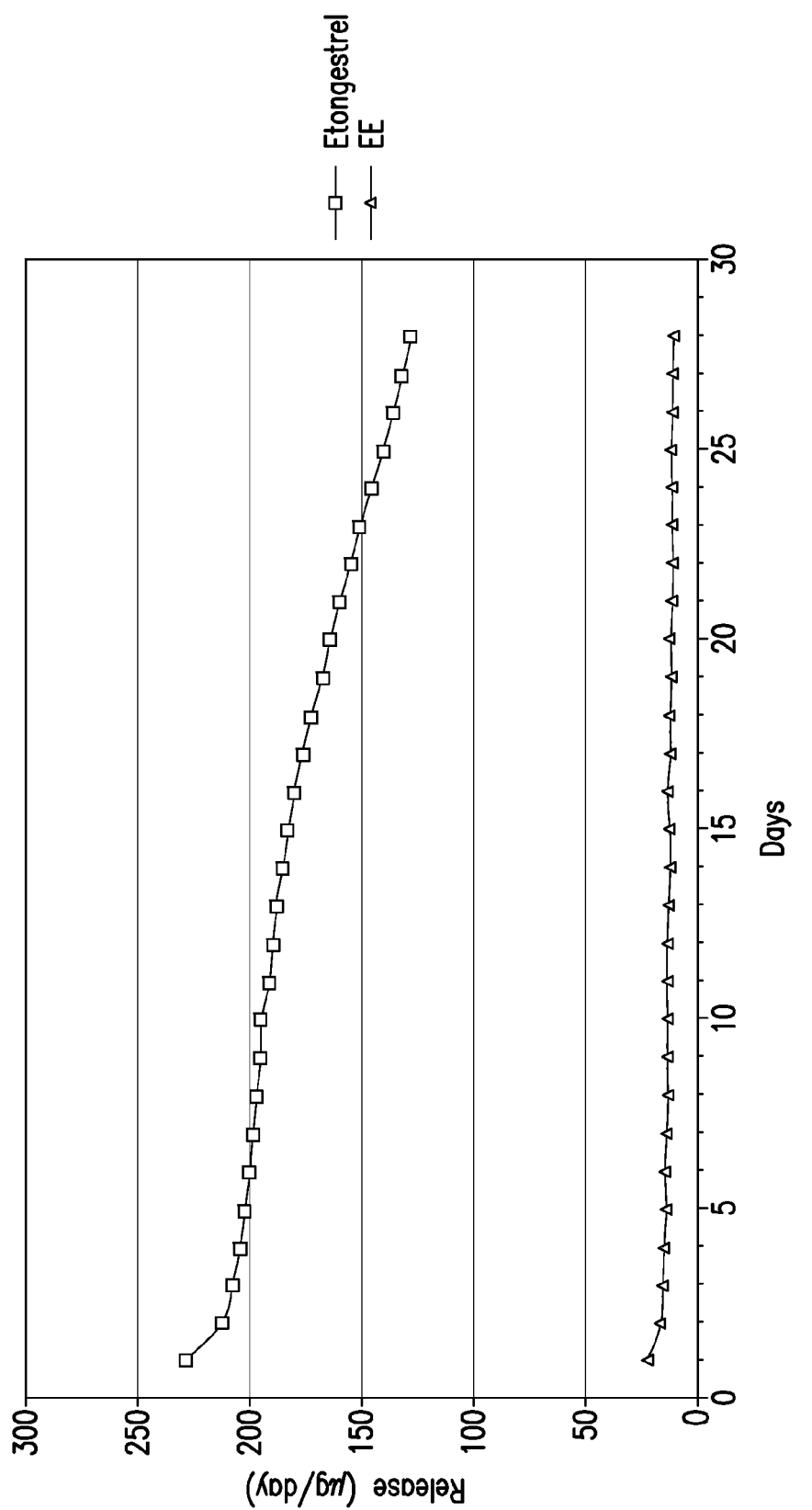
Figure 11:
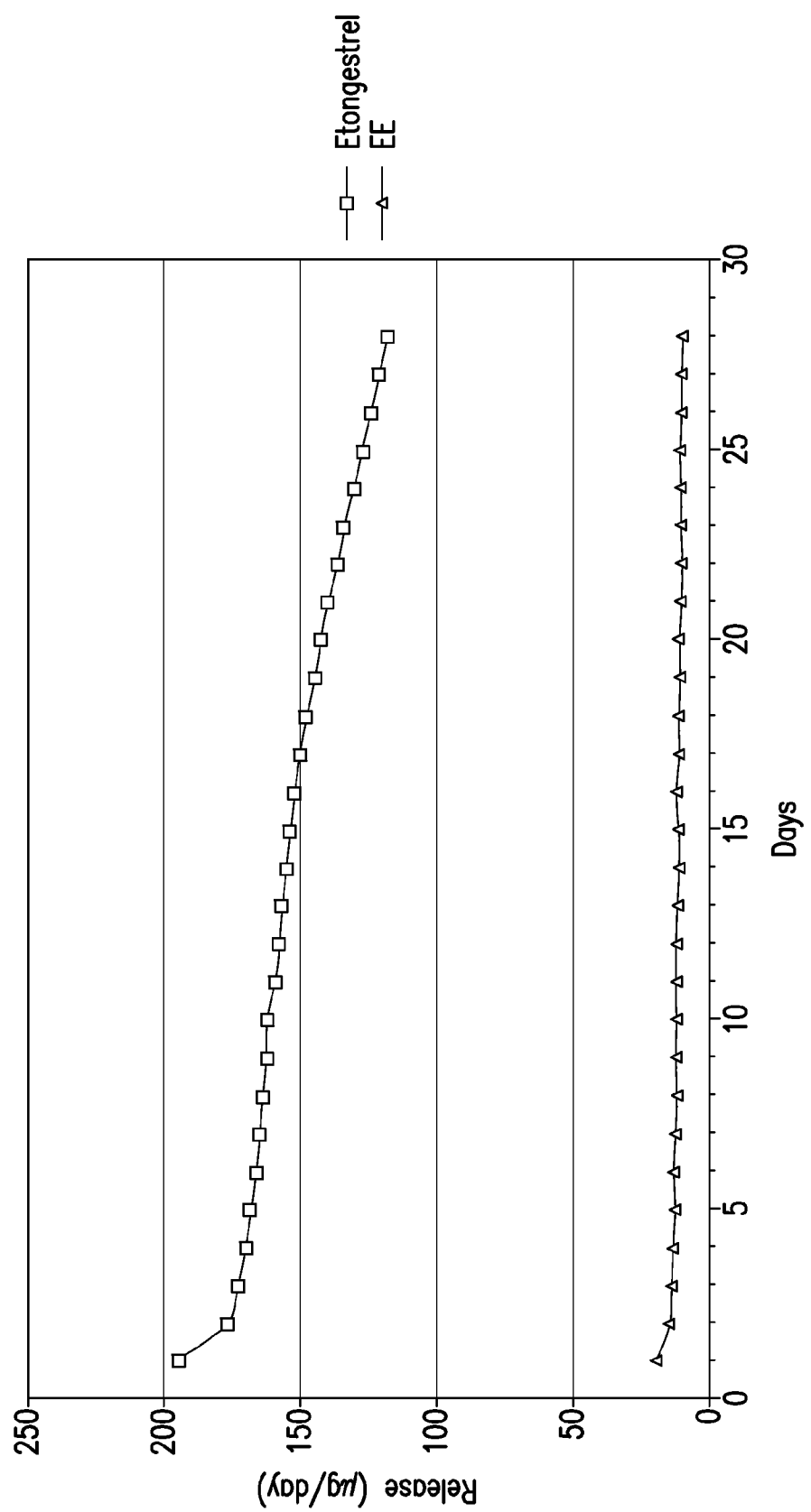
Figure 12:
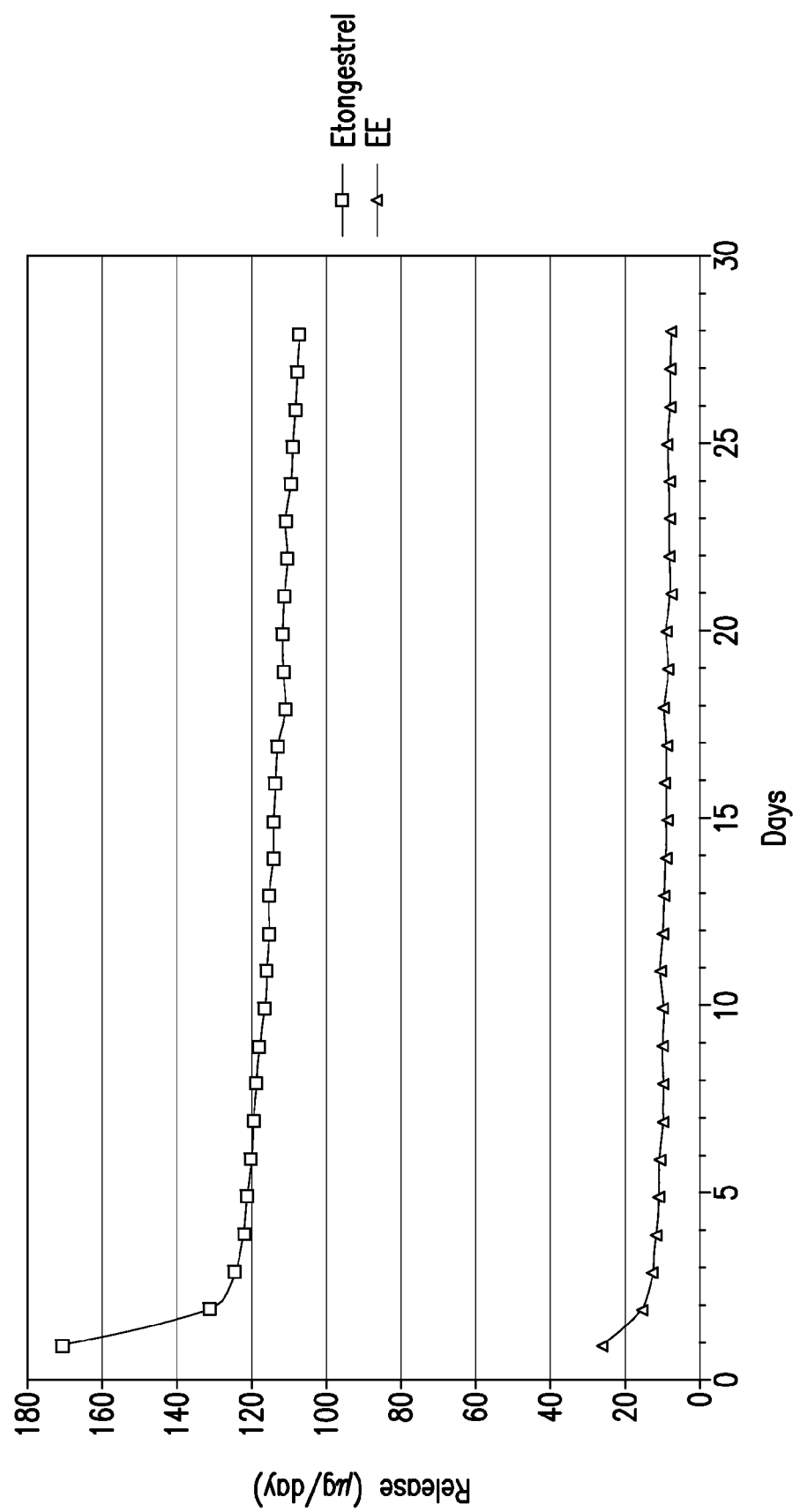
Figure 13:
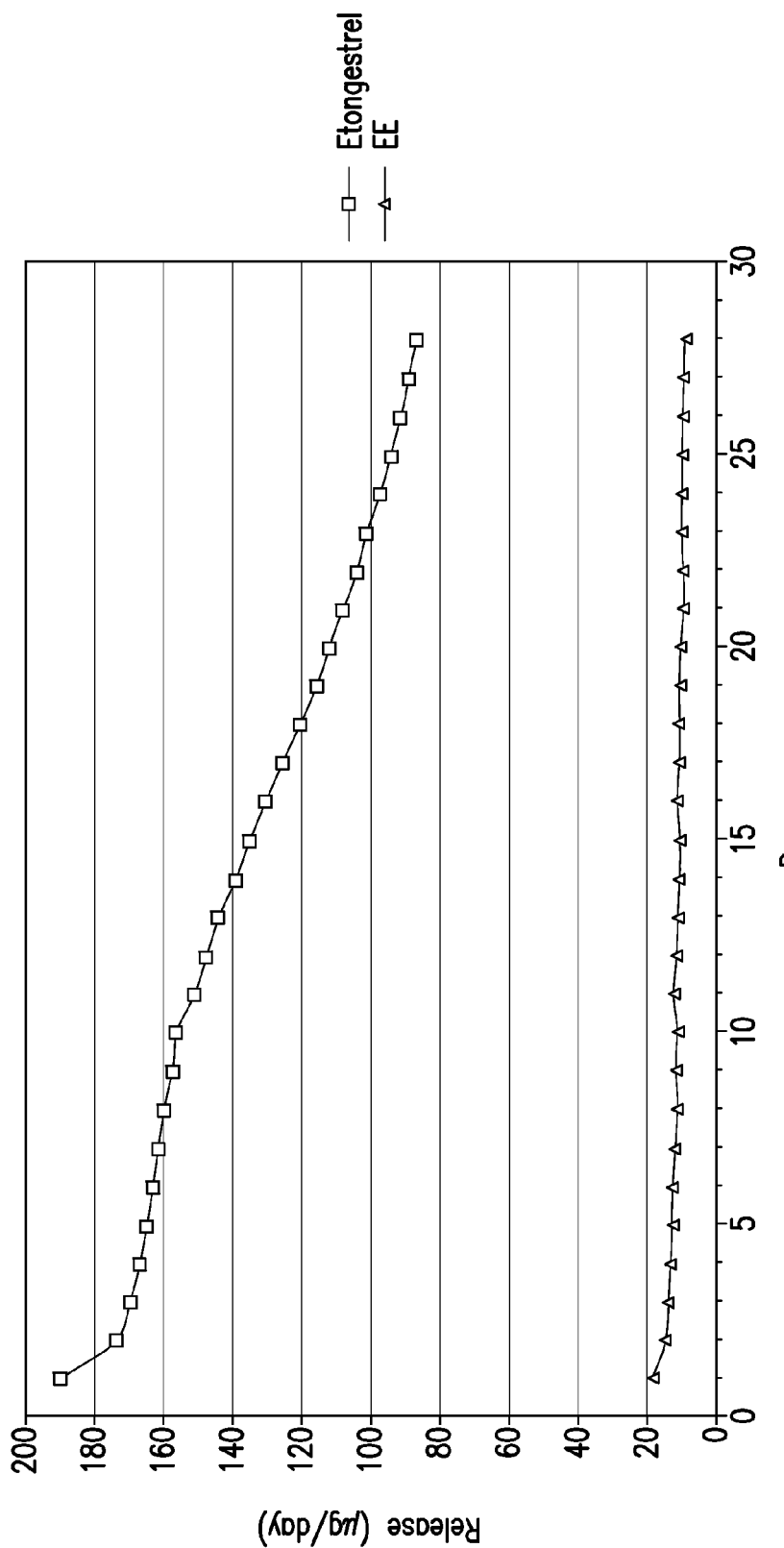
Figure 14:
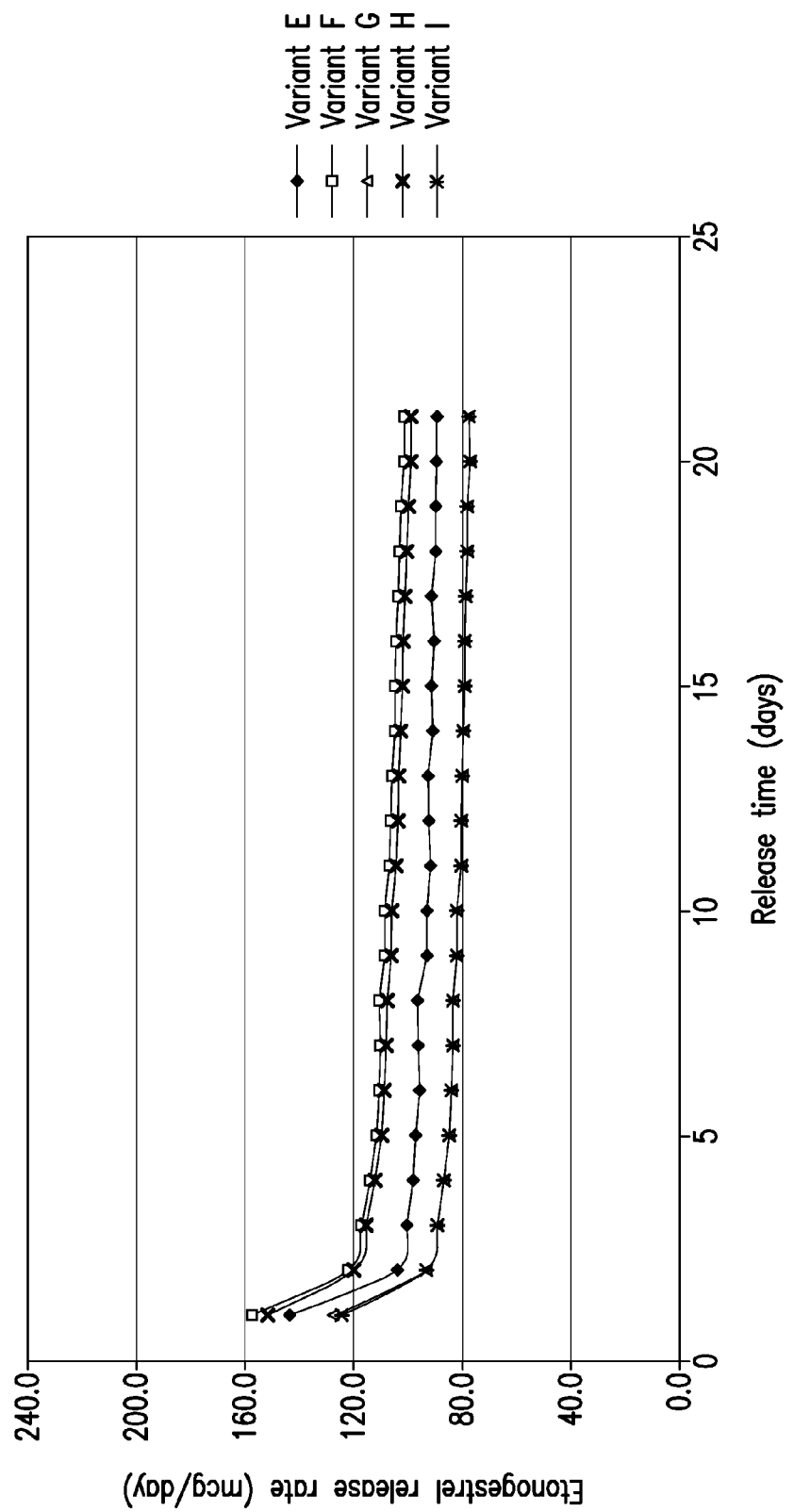
Figure 15:
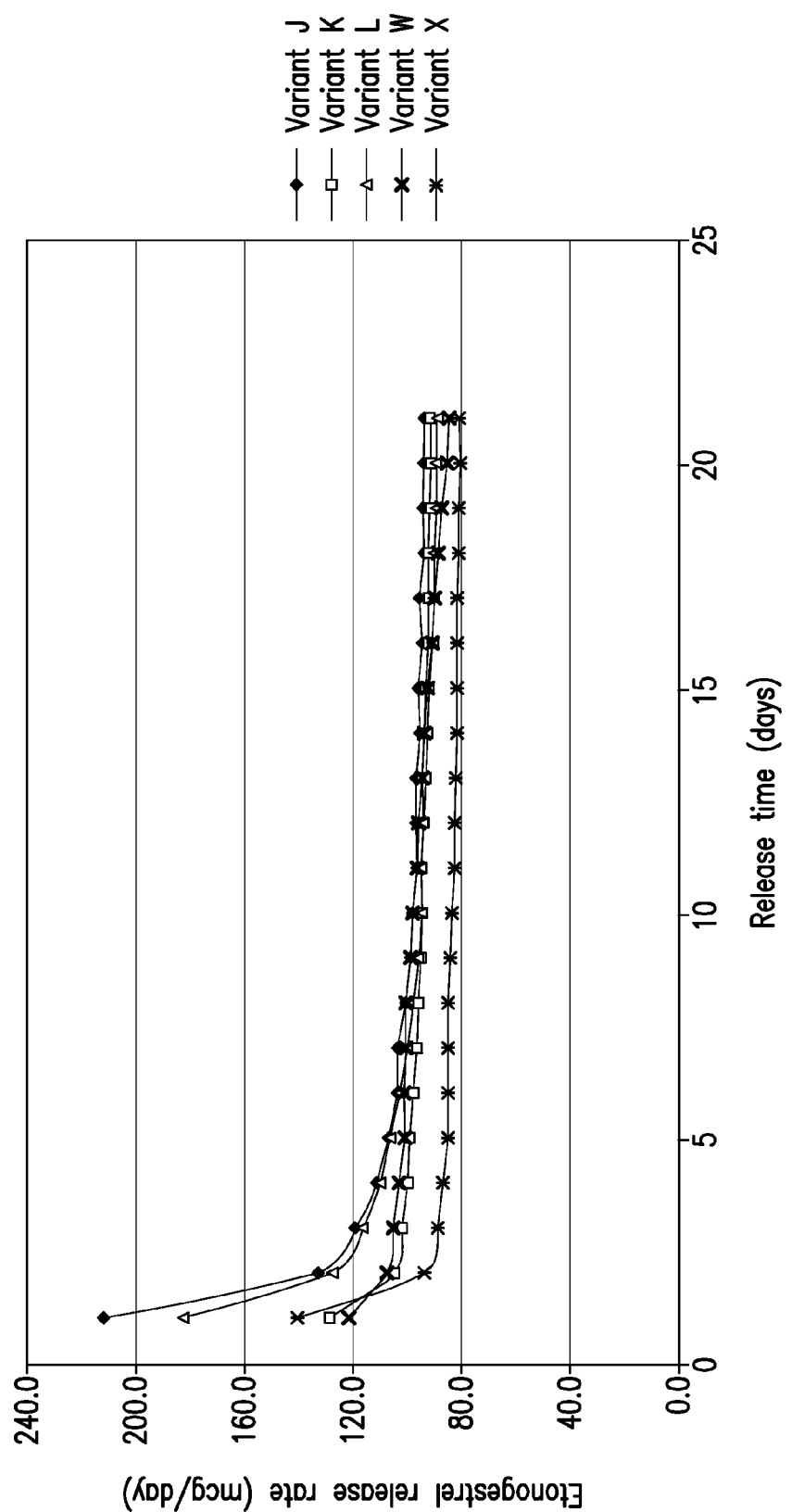
Figure 16:
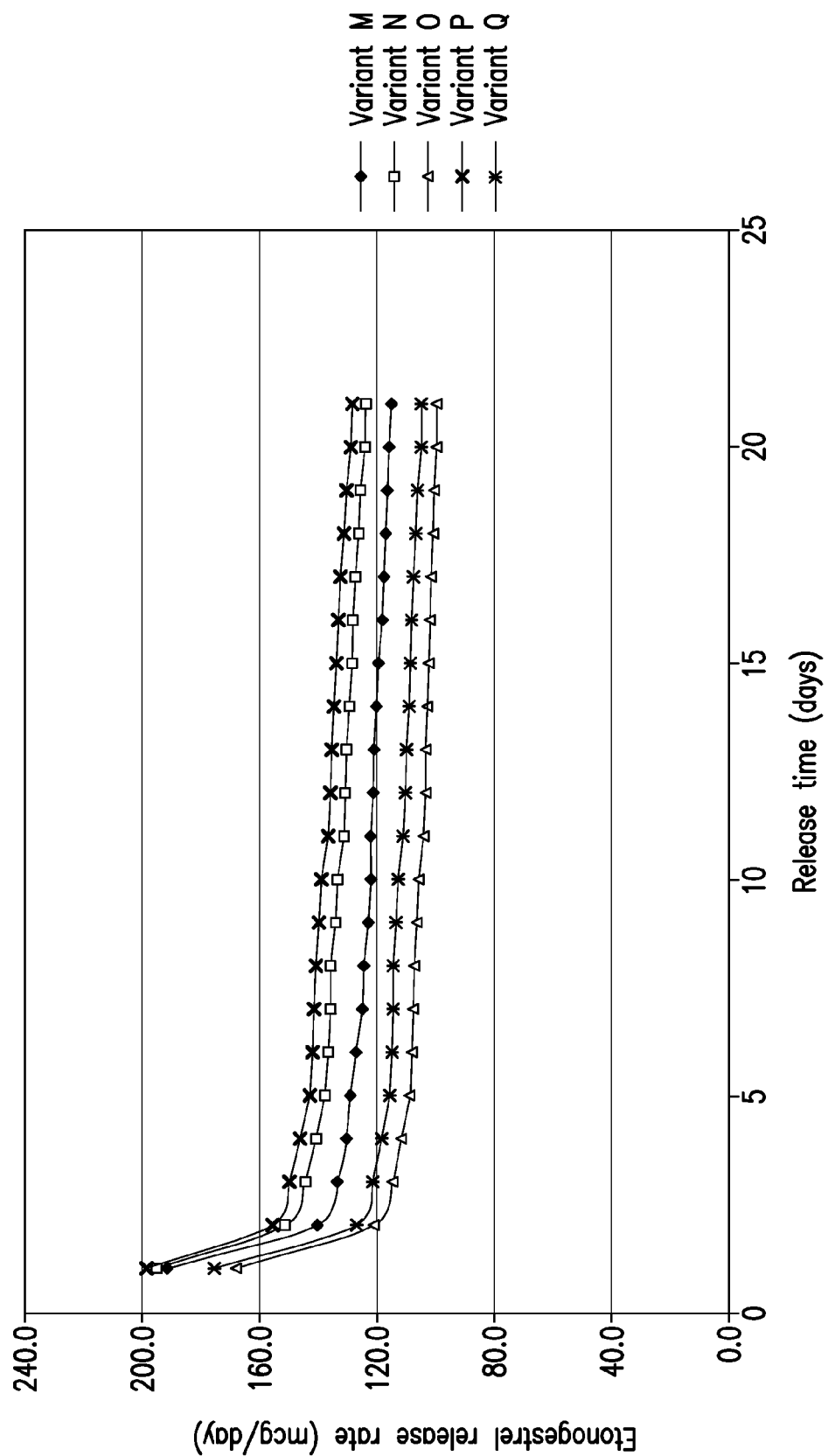
Figure 17:
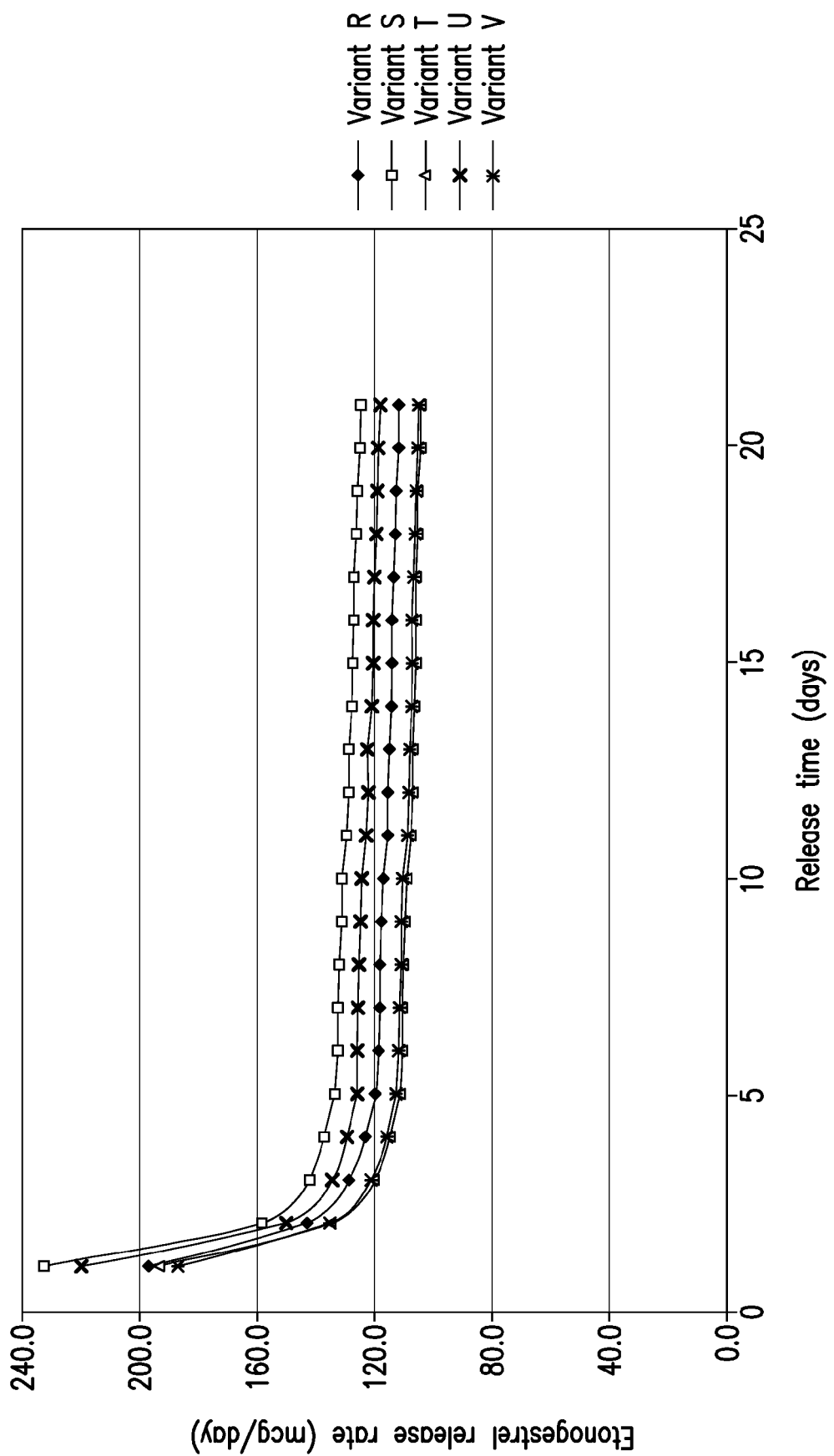
Figure 18:
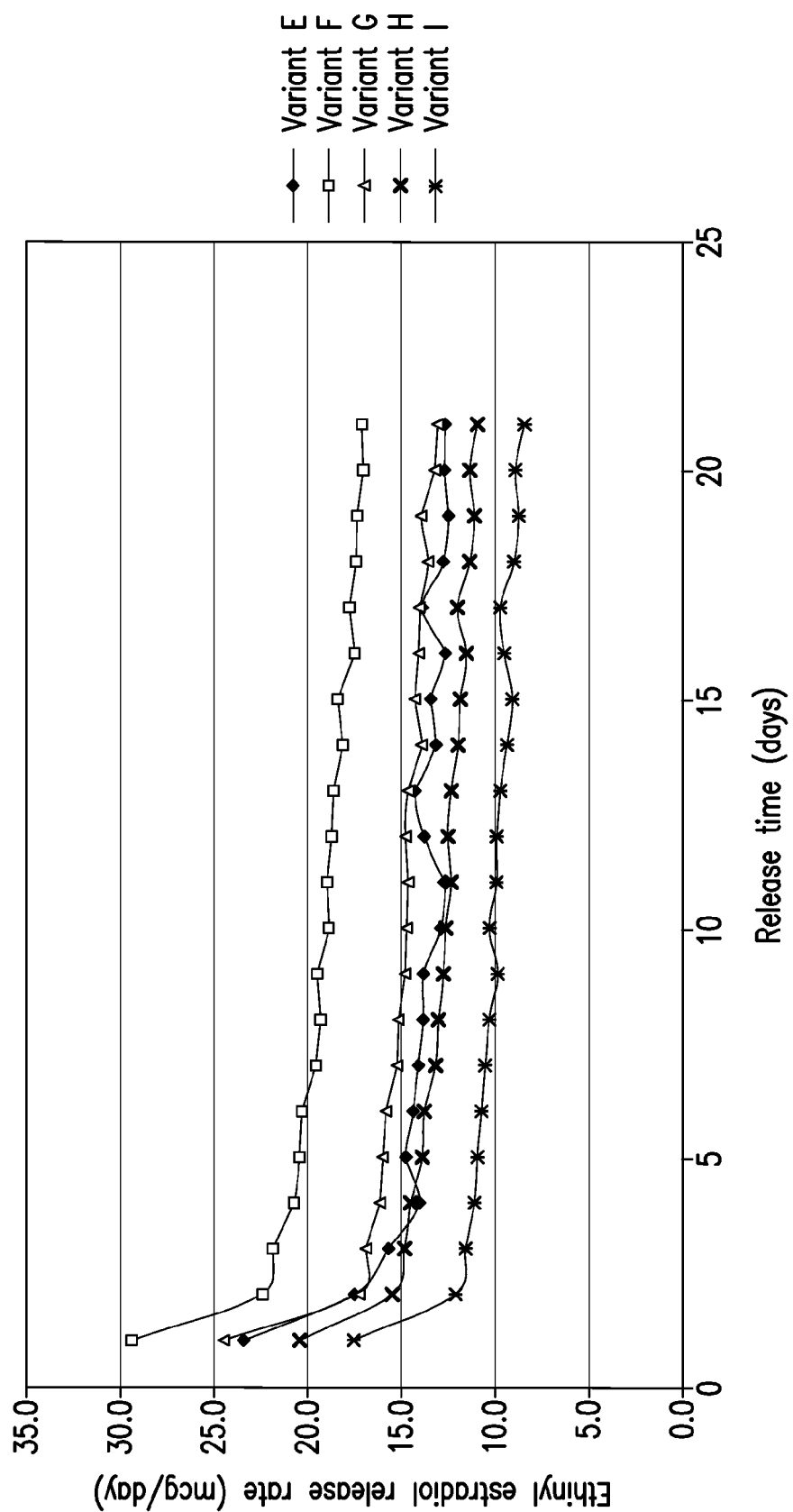
Figure 19:
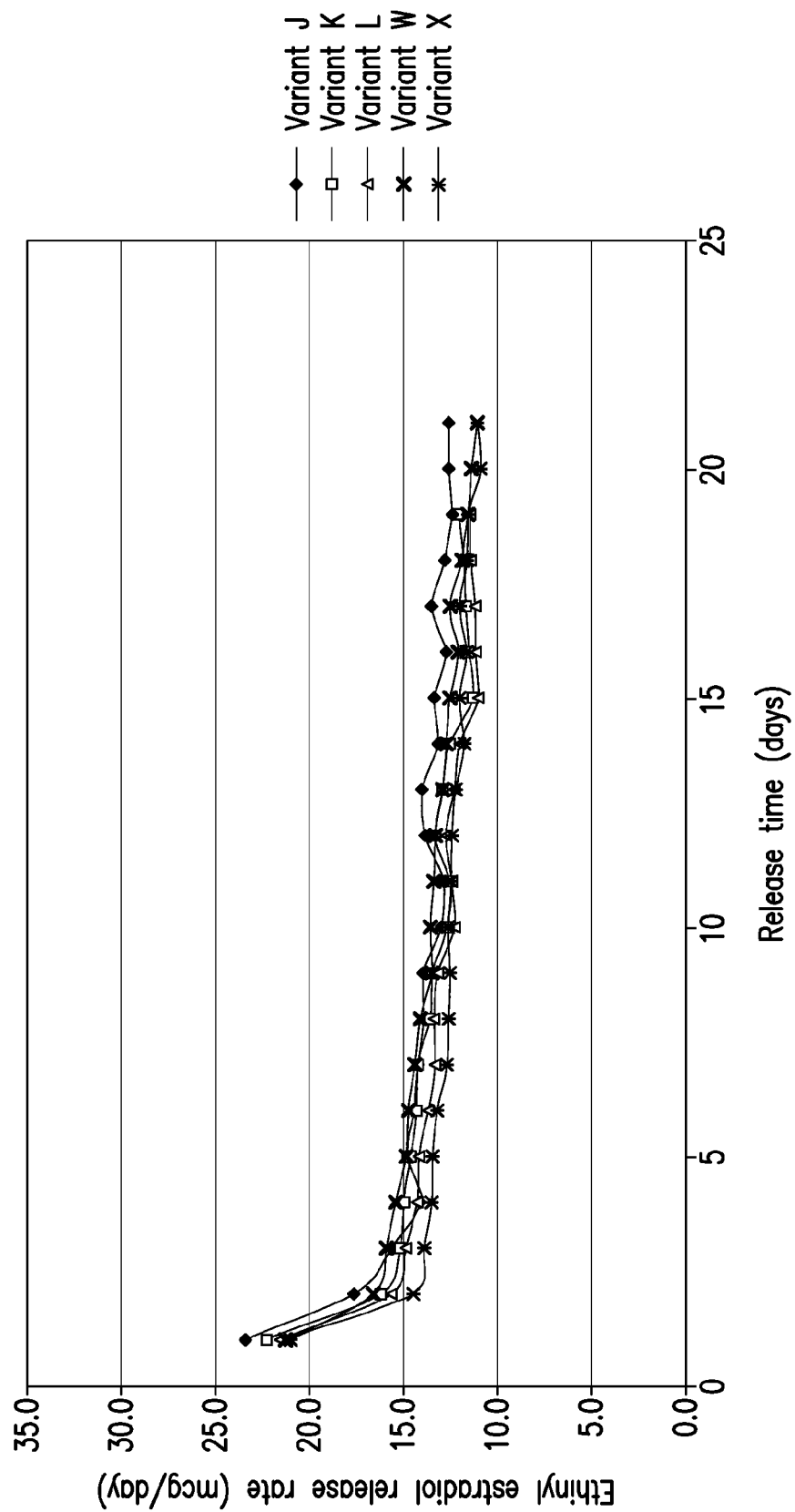
Figure 20:
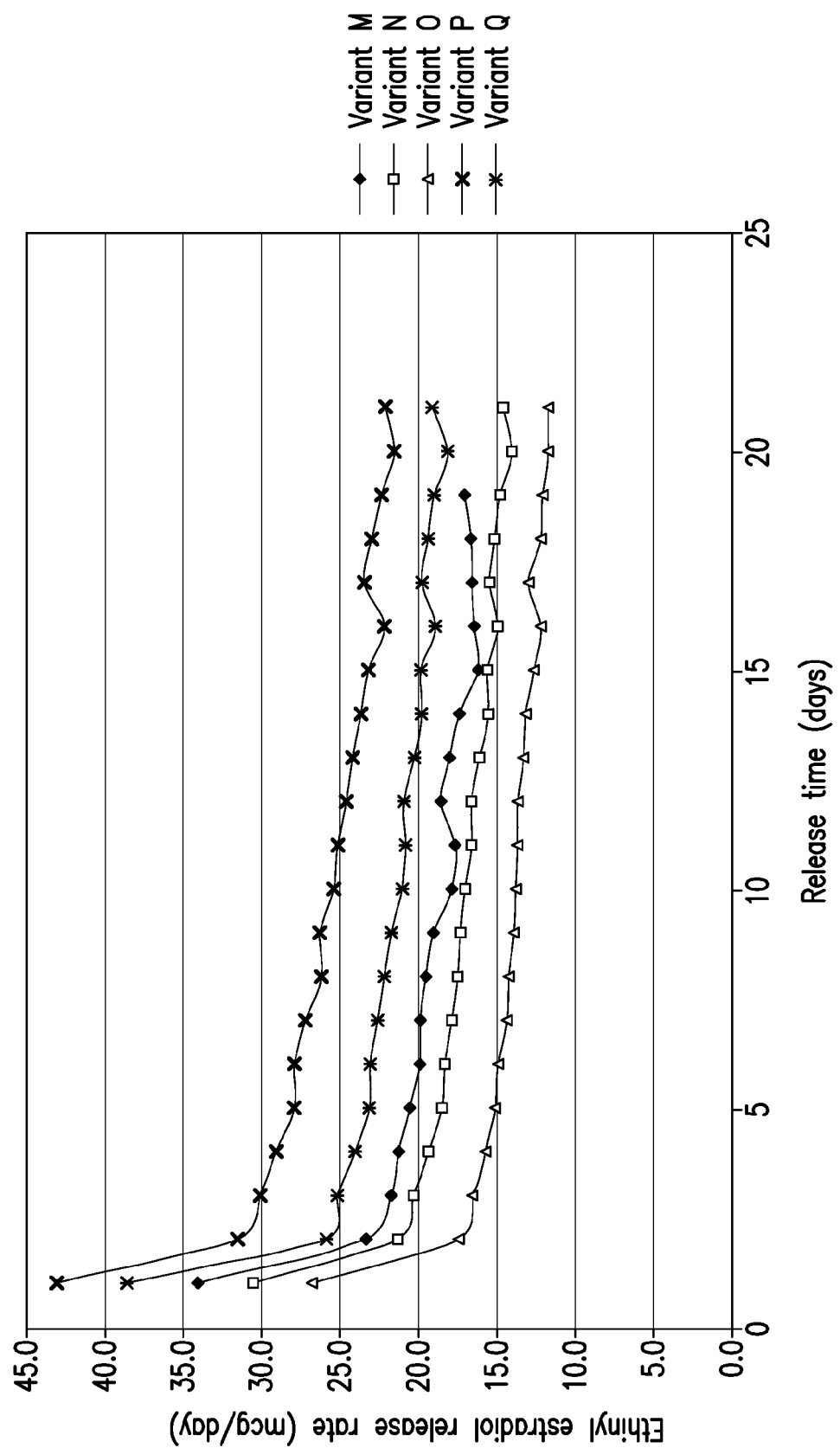

FIG. 3:
In vitro release rates of ethinyl estradiol (EE) for all 4.0 mm batches.
FIG. 4:
In vitro release rates of ethinyl estradiol for all 3.5 mm batches.
FIG. 5:
Schematic description of a vaginal ring of the subject invention.
FIG. 6:
In vitro-release rates of etonogestrel and ethinyl estradiol from one A1 ring.
FIG. 7:
In vitro-release rates of etonogestrel and ethinyl estradiol from one A2 ring.
FIG. 8:
In vitro-release rates of etonogestrel and ethinyl estradiol from one A3 ring.
FIG. 9:
In vitro-release rates of etonogestrel and ethinyl estradiol from one A4 ring.
FIG. 10:
In vitro-release rates of etonogestrel and ethinyl estradiol from one B1 ring.
FIG. 11:
In vitro-release rates of etonogestrel and ethinyl estradiol from one B2 ring.
FIG. 12:
In vitro-release rates of etonogestrel and ethinyl estradiol from one B3 ring.
FIG. 13:
In vitro-release rates of etonogestrel and ethinyl estradiol from one B4 ring.
FIG. 14:
In vitro release rates of etonogestrel for fibre variants E, F, G, H and I.
FIG. 15:
In vitro release rates of etonogestrel for fibre variants J, K, L, W and X.
FIG. 16:
In vitro release rates of etonogestrel for fibre variants M, N, O, P and Q.
FIG. 17:
In vitro release rates of etonogestrel for fibre variants R, S, T, U and V.
FIG. 18:
In vitro release rates of ethinyl estradiol for fibre variants E, F, G, H and I.
FIG. 19:
In vitro release rates of ethinyl estradiol for fibre variants J, K, L, W and X.
FIG. 20:
In vitro release rates of ethinyl estradiol for fibre variants M, N, O, P and Q.
FIG. 21:
In vitro release rates of ethinyl estradiol for fibre variants R, S, T, U and V.

DETAILED DESCRIPTION OF THE INVENTION

Fick's law of diffusion governs the release of compounds, such as contraceptive steroids from a ring. According to this law, the amount of mass transferred over the boundary is an inverse function of the distance across the boundary. In a two-layer design, the steroid nearest to the outer layer (the skin) will diffuse first and this results in depletion of the outer core and hence the diffusion distance will increase. The depletion of the outer core layer and the resulting increase of the diffusion distance will result in a decrease of the release rate. When speaking about the release rate of one drug substance, the problem of depletion and increase of the diffusion distance can be overcome by concentrating the drug substance in an intermediate layer between a placebo skin and a placebo core. Since the drug substance is then concentrated in a relatively thin layer, lengthening of the diffusion distance during release is minimal, resulting in a more constant release rate over time.

The release rate of a cylindrical reservoir/membrane design is:

$$\frac{dM}{dT} = \frac{2\pi L D_p K_{p/s} \Delta C}{\mathrm{Ln}(r_0/r_1)}$$

L=the length of the cylinder
$D_p$=the diffusion co-efficient of the compound in a skin polymer
$K_{p/s}$=partition coefficient of the steroid between the skin and core polymer
$\Delta C$=the difference in concentration between the core (or intermediate layer) and the sink
$r_0$=is the overall radius, i.e. the radius of the cylinder including the skin
$r_1$=is the radius of the core The equation shows that zero order release is obtained when the term on the right hand side of the equation is constant, i.e. not a function of time. Lengthening of the diffusion distance due to depletion of the core is insignificant in a three-layer design containing one drug substance and hence the term $(r_0/r_1)$ may be considered almost constant. In case the steroid in the intermediate layer is present in the dissolved state, the concentration gradient ($\Delta C$) will steadily decrease in time and consequently the release rate dM/dt will decrease (deviate from zero order release kinetics).

The subject invention provides a drug delivery system comprising at least two active drug substances.

The subject invention provides a drug delivery system, typically a substantially ring-shaped form intended for vaginal administration, which comprises at least one compartment consisting of (i) a thermoplastic polymer core, (ii) a thermoplastic polymer intermediate layer and (iii) a thermoplastic polymer skin covering the intermediate layer, wherein said intermediate layer comprises (a) crystals of a first pharmaceutically active compound and (b) a second pharmaceutically active compound in dissolved state and wherein said core comprises said second compound as well, optionally in the same concentration as in the intermediate layer.

The essence of this novel three-layered ring of the subject invention lies in the provision of the possibility to adjust the release rates of more than one pharmaceutically active compound independently from each other while maintaining the physical stability of the ring at room temperature.

This is accomplished by (1) incorporating crystalline reservoirs of the (first) compound in the intermediate layer of the ring, (2) loading both the intermediate layer and the core of the ring with the second compound in dissolved form, thereby enlarging the compound reservoir, and (3) defining the thickness of the skin of the ring.

In a specific embodiment of the subject invention, the compounds are steroids. For the sake of ease, we hereinafter refer to steroids, although also non-steroidal compounds are contemplated by the subject invention as well.

The steroid molecules incorporated in the crystalline lattice are in dynamic equilibrium with the steroid dissolved in the polymer of the intermediate layer. When no diffusion occurs, the steroid concentration in the polymer will equal or come close to the equilibrium concentration. After the ring has been put in a sink, steroid will start to diffuse out of the ring and the concentration of the steroid dissolved in the polymeric intermediate layer will drop slightly. As a consequence thereof, the steroid crystals will start to dissolve. Thus, the decrease of the concentration gradient due to diffusive transport out of the ring is counterbalanced by the steroid in the crystalline reservoir. FIGS. 1 and 2 illustrate this stabilizing effect of crystals in the intermediate layer. In the beginning, the slope of the release curve is very flat, i.e. indicates that the release is almost zero order up to day 10. Then, after day 10, the release curve suddenly becomes much steeper, i.e. the release rate becomes more time dependent (less zero order). Apparently this moment coincides with the moment that the size and amount of crystals in the polymer matrix has decreased beyond a certain point and from this point on the loss of steroid due to diffusion outside the ring can no longer be adequately counterbalanced by crystals going into dissolution. When the majority of crystals are dissolved the concentration gradient is no longer stabilized and hence a steeper curve is seen. The stabilization of the concentration gradient by this mechanism functions when the dissolving of the steroid crystals proceeds fast compared to the loss of steroid due to diffusion. So, the concentration drop is counter balanced to a certain extent, and the net effect will be zero provided the crystals dissolve relatively fast in the polymer.

In other words, the subject three-layer design is a three-layered ring comprising at least one compartment consisting of (i) an intermediate layer loaded with two steroids, one (steroid A) partly present in the crystalline phase and partly dissolved in the polymer and the other (steroid B) entirely dissolved in the polymer, (ii) a core loaded with steroid B (entirely dissolved and optionally in the same concentration as in the intermediate layer) and (iii) a placebo skin.

In the subject three-layered ring, steroid B is not only accommodated in the intermediate layer, but also in the core. In one embodiment of the subject invention, the concentration of steroid B is the same in the core and in the intermediate layer.

By loading both core and intermediate layer with steroid B, the reservoir for steroid B is largely increased, allowing a fairly constant release rate of this steroid over a prolonged period (see FIGS. 3 and 4). As a result of this design, the release rate of steroid A and the release rate of steroid B can be adjusted independently from each other. Moreover, by loading the core with steroid B, also back-diffusion of steroid B from the intermediate layer back to the core is prevented. Back-diffusion of steroid B would lead to a steadily decreasing concentration in the intermediate layer and thus a decreasing release profile upon storage (until even distribution of steroid B in core and intermediate layer). Also steroid A may back-diffuse into the core. This is however less critical since the concentration of steroid A in the intermediate layer is stabilized because of its presence in crystalline form. In a special embodiment of the subject invention, steroid A, in dissolved form, can however also be loaded into the core. This will reduce (or eliminate) internal diffusion effects.

Thus, the concept of this three-layer vaginal ring is to concentrate steroid in a relatively thin intermediate layer wherein part thereof will be present in the form of crystals dispersed in the thin intermediate layer. The desired release rate of steroid A is obtained by adjusting the skin thickness. Therefore, steroid A is incorporated in crystalline form and steroid B in dissolved form thereby making it possible to adjust the concentration of steroid B to the already pre-set skin thickness. Since the volume of the intermediate layer may be relatively small, this approach may lead to a relatively small content and may become depleted relatively fast. A possible too fast depletion of the three-layered ring is prevented by loading the core with the second steroid (B) as well.

In a different embodiment of the subject invention, the drug delivery system is a three-layered vaginal ring comprising at least one compartment consisting of (i) an intermediate layer loaded with steroid A partly present in the crystalline phase and partly dissolved in the polymer and (ii) a core loaded with steroid B which is entirely dissolved in the polymer and (iii) a placebo skin. This ring design, although containing only one steroid in the intermediate layer (as opposed to two steroids in the ring design described above), will, after some time, turn into the same design as the ring described above wherein there are two steroids in the intermediate layer. This is because over a period of time, steroid B will diffuse into the intermediate layer and at a particular point in time will contain (i) an intermediate layer medicated with two steroids, one (steroid A) partly present in the crystalline phase and partly dissolved in the polymer and the other (steroid B) entirely dissolved in the polymer, (ii) a core loaded with steroid B (entirely dissolved) and (iii) a placebo skin.

The vaginal ring of the subject invention can be manufactured by the known process of extrusion, such as co-extrusion and/or blend-extrusion. The drug-loaded core, the drug-loaded intermediate layer and the non-medicated outer layer are all co-extruded. The fibres thus obtained are cut into pieces of the required length and each piece is assembled to a ring-shaped device in any suitable manner. The rings are then packed for example in a suitable sachet, optionally after being sterilized or disinfected.

The thermoplastic polymer that can be used in practising the invention, may in principle be any thermoplastic polymer or elastomer material suitable for pharmaceutical use, such as low density polyethylene, ethylene-vinylacetate copolymers and styrene-butadiene-styrene copolymers. In a specific embodiment, ethylene-vinylacetate copolymer (poly-EVA) is used due to its excellent mechanical and physical properties (e.g. solubility of the steroids in the material). The poly-EVA material may be used for the core, the intermediate layer as well as the skin and can be any commercially available ethylene-vinylacetate copolymer, such as the products available under the trade names: Elvax, Evatane, Lupolen, Movriton, Ultrathene, Ateva and Vestypar.

In one embodiment both core and intermediate layer are made out of the same polymer grade. In another embodiment, the core and the intermediate layer are not made out of the same polymer grade in order to allow for further flexibility of the ring. By electing different polymer grades for the core and the intermediate layer, fine-tuning of the flexibility of the ring is possible.

The vaginal ring according to the invention can be manufactured in any size as required. In one embodiment, the ring has an outer diameter (outer circumference) of between 50 and 60 mm and in another embodiment between 52 and 56 mm; the cross sectional diameter is between about 2.5 and 5 mm, in a specific embodiment between about 3.0 and 4.5 mm, and in another embodiment between about 3.5 and 4.0 mm and in yet another embodiment is 4.0 mm.

It is also an object of the subject invention to provide an improved vaginal ring in which the intermediate layer and/or the core, in addition to steroids for contraception or hormone replacement, also comprises anti-microbials, e.g. to concomitantly treat and/or prevent sexually-transmitted diseases (STD's) such as HIV, herpes, chlamydia and gonorrhoea.

In the subject invention, the surface of the core body is more than 800 mm², and in another embodiment more than 1000 mm² and will typically be in the order of 1700-2200 mm², though significantly larger surfaces are possible, provided that the design (physical dimensions) of the vaginal ring prevents inconvenience for the subject. It may sometimes be required to add a second compartment which is a placebo compartment or a compartment loaded with one or more other drugs. Such an extra compartment may be necessary for example in practising hormonal replacement therapy, where the ratio between progestogen and estrogen is different from the ratio suitable for contraception. Such an extra compartment can also be necessary to administer, in addition to the steroids, anti-microbial drugs to treat and/or prevent STD's such as AIDS, chlamydia, herpes and gonorrhoea.

Any anti-microbial drug can be incorporated into a vaginal ring of the subject invention (in the intermediate layer and/or in the core and/or in an additional compartment). The anti-microbial drug can be any anti-bacterial drug such as any antibiotic, any anti-viral agent, any anti-fungal agent or any anti-protozoal agent. An example of an anti-microbial drug contemplated to be incorporated into the vaginal ring of the subject invention is mandelic acid condensation polymer (Zanefeld et al. (2002), *Fertility and Sterility* 78(5): 1107-1115). Another example is dapivirine (4-[[4-[2,4,6-trimethylphenyl)amino-2-pyrimidinyl]amino]benzonitrile).

FIG. 5 shows a schematic description of the vaginal ring of the subject invention. $R_1$ is the diameter of the three-layered fibre. $R_2$ is the radius of the core together with the intermediate layer and $R_3$ is the radius of the core. The ratios of $R_1/R_2$ and $R_2/R_3$ described in that figure are defined as follows:

| Ranges | $R_1/R_2$ | $R_2/R_3$ |
| --- | --- | --- |
| Embodiment 1 | 1.0075-2.0000 | 1.0075-2.0000 |
| Embodiment 2 | 1.0100-1.5000 | 1.0200-1.5000 |
| Embodiment 3 | 1.0300-1.3000 | 1.0200-1.5000 |
| Embodiment 4 | 1.0400-1.1800 | 1.0200-1.0500 |
| Embodiment 5 | 1.0300-1.2000 | 1.0100-1.0900 |

As used herein, "room temperature" lies anywhere between about 18° C. and about 30° C.

As used herein, a physically stable drug delivery system (ring) is a system which can be stored at about 18° C.-30° C. for at least about one and a half (1.5) year without steroid crystal formation on the surface of the skin of the vaginal ring.

The vaginal ring according to the invention is primarily designed for contraceptive use, but—as said above—may also be used under certain conditions in HRT (hormonal replacement therapy).

The vaginal ring of the subject invention may—as said above—also be used to concomitantly provide contraception and combat microbial disease. The microbial infection to be treated and/or prevented can be any bacterial, viral, fungal or protozoal infection. Specifically, sexually transmitted diseases such as HIV, chlamydia, gonorrhoea, or herpes may be treated by incorporation of an anti-microbial agent into the ring of the subject invention.

It is a further object of the invention to provide a method of contraception which comprises the steps of positioning a drug delivery system of the subject invention within the female vaginal tract and retaining the system within the vaginal tract for at least approximately 21 days.

It is another object of the subject invention to provide a method of concomitantly providing contraception and treating or preventing a sexually transmitted disease which comprises the steps of positioning a drug delivery system of the subject invention within the female vaginal tract and retaining the system within the vaginal tract for at least approximately 21 days.

In one embodiment, the drug delivery system is removed after about 21 days for an approximate one week period to permit menstruation. In other embodiments, the drug delivery system is removed after about 42, 63, 84, 105, 126, 147, 186, 189, 210, 231, 252, 273, 294, 315, 336 or 357 days for an approximate one week period to permit menstruation. After the approximate week to allow for menstruation, a new drug delivery system of the subject invention is inserted into the female vagina to provide contraception in the next female cyclus or cyclusses.

The subject invention further envisions a use of a drug delivery system of the subject invention for the manufacture of a contraceptive kit.

The subject invention further encompasses a use of a drug delivery system of the subject invention for the manufacture of a medicament for hormone replacement therapy.

The subject invention also provides a use of a drug delivery system of the subject invention for the manufacture of a combination preparation to provide contraception and to treat and/or prevent a sexually transmitted disease such as for example AIDS, herpes, chlamydia and gonorrhoea.

The progestogenic steroidal compound of the subject invention can be any suitable progestogen, such as desogestrel, etonogestrel, levonorgestrel, norgestimate, gestodene or any other steroidal compound with progestogenic activity. The estrogenic steroidal compound can be any suitable estrogen, such as estradiol, estriol, mestranol and ethinylestradiol. In a specific embodiment of the subject invention, the progestogen is etonogestrel. In a specific embodiment of the subject invention the estrogen for contraceptive use is ethinylestradiol. In another embodiment, estradiol is the estrogen used for HRT.

In one embodiment of the subject invention, ethinyl estradiol is present in the intermediate layer and in the core at about 0.05-1.5% by weight. In other embodiments, ethinyl estradiol is present in the intermediate layer and in the core at about 0.08-0.5% by weight, at about 0.09-0.20% by weight, at about 0.09-0.18% by weight or at about 0.09-0.15% by weight.

In one embodiment of the subject invention, etonogestrel is present in the intermediate layer at about 6-80% by weight. In other embodiments, etonogestrel is present in the intermediate layer at about 6-70% by weight, at about 10-53% by weight, at about 10-30% by weight, at about 10-15% by weight, or at about 10-12% by weight.

The subject invention also provides a method of manufacturing the three-layered drug delivery system of the subject invention by:
(i) Producing a loaded (medicated) homogenous polymer core granulate and a loaded (medicated) homogenous polymer intermediate layer granulate;
(ii) Co-extruding the core granulate and the intermediate layer granulate with a polymer skin granulate to form the three-layered drug delivery system.

The production of the loaded (medicated) homogenous polymer core granulate and loaded (medicated) homogenous polymer intermediate layer granulate comprises:
(a) grounding the polymer;
(b) dry powder mixing the grounded polymer with the active compounds to be loaded in the intermediate layer;
(c) dry powder mixing the grounded polymer with the active compound to be loaded in the core;

(d) blend extruding the resulting powder mixtures of steps (b) and (c);

(e) cutting the resulting loaded polymer strands into granules, thereby obtaining a core granulate and an intermediate layer granulate;

(f) lubricating both core granulate and intermediate granulate with a lubricant;

wherein steps (b) and (c) are interexchangeable.

The present invention is further described in the following examples which are not in any way intended to limit the scope of the invention as claimed.

EXAMPLES

Example 1

Preparation of the Three-Layered Ring

Eight (8) three-layer fibres were prepared (A1-A4 and B1-B4). The fibres were stretched to 3.5 mm (Bx) and 4.0 mm (Ax) from a single capillary (4.1 mm).

In order to mix the active ingredients etonogestrel (steroid A) and ethinyl estradiol (steroid B) homogeneously through the polymer, two subsequent mixing steps were performed. In the first step, dry powder mixing was performed with the micronized active compounds and polymer powder. These micronized compounds were mixed with polymer powder in a stainless steel drum using a Rhönrad (Barrel-hoop principle) with a fixed rotation speed of approximately 26 rpm for 60 minutes. This first powder mixing step was performed to mix polymer and active compounds for both the core (polymer powder and micronized ethinyl estradiol) as well as for the intermediate layer (polymer powder, micronized ethinyl estradiol and micronized etonogestrel). Subsequently the homogenized powder mixture was blend extruded using a 25 mm co-rotating double screw blend extruder (Berztorff ZE25) and the resulting medicated polymer strands were cut into granules using an Scheer granulator. According to this process a batch core granulate and a batch intermediate layer granulate were manufactured. After granulation these batches were lubricated with magnesium stearate in order to facilitate the next processing step (co-extrusion). The composition of the granulate batches that was used to manufacture the tri-layer fibre, using a co-extrusion process, are described in Table 1 below.

TABLE 1

| Material | Composition | |
|---|---|---|
| | Core granulate | Intermediate layer granulate |
| Etonogestrel | — | 10.3% |
| Ethinyl estradiol | 0.095% | 0.092% |
| Evatane 28-25 | 99.8% | 89.5% |
| Magnesium Stearate | 0.1% | 0.1% |
| Total | 100.0% | 100.0% |

Tri-Layer Co-Extrusion

A Plastic Machinenbau co-extruder ($^{15}/_{18}$ mm) in combination with an EX10, Fourné (10 mm) extruder was used for trico-extrusion. The 18 mm and the 15 mm Plastic Machinenbau extruders processed the core and the intermediate layer respectively and the 10 mm Fourné extruder was used to process the skin (outer layer). The three extruders were connected with a 3-compartment spinning block (Ankutec, Germany) with 3 separate spinning pumps (to control the volume flow rate (melt flow) of each layer). The three melt flows were combined in a spinneret resulting in a fibre with 3 layers. A capillary of 4.1 mm was used. All fibres were extruded at an extrusion temperature of 110° C.

The spinning rate was tuned to obtain the desired fibre diameter, either 3.5 mm or 4.0 mm, and the desired layer thickness for skin and intermediate layer was obtained by adjustment of the spinning pumps. Each of the tri-layer fibre variants was produced by using the appropriate spinning rate and spinning pump settings (totally 2×4 variants, A1-A4 and B1-B4). After approximately 20 minutes tri-layer co-extrusion of each variant, the tri-layer fibre was collected on a stainless steel reel for 30 minutes. The outer diameter of the fibre was measured on-line continuously using a laser micrometer and recorded. At the start and at the end of these 30 minutes, the diameter of the fibre, thickness of the middle layer, thickness of the skin was measured and recorded.

The loaded fibres were processed at an extrusion speed of 3 m/min for variants A and 3.9 m/min for variants B. Except variant 3 which was processed at 1.0 m/min for the fibre A3 and 1.3 m/min for the fibre B3.

Fibre Dimensions

The fibre dimensions (outer diameter, intermediate layer thickness and skin thickness) were determined directly after processing and on 10 assembled rings. The outer diameter was determined by means of laser thickness gauge (Mitutoyo). The intermediate layer and skin thickness were determined using a microscope (Jena). The results for the loaded batches are shown in Tables 2a and 2b.

TABLE 2a

Fibre dimensions of 4.0 mm loaded fibres processed at an extrusion speed of 3 m/min (except variant A3, which was processed at 1 m/min)

| Variant | Fibre diameter [mm] | Intermediate layer [μm] | Skin [μm] | Skin polymer | R1/R2 | R2/R3 |
|---|---|---|---|---|---|---|
| A1 | 4.00 | 67 | 66 | Evatane 1020 VN3 | 1.0341 | 1.0359 |
| A2 | 4.00 | 61 | 81 | Evatane 1020 VN3 | 1.0422 | 1.0328 |
| A3 | 3.99 | 67 | 294 | Evatane 1040 VN4 | 1.1728 | 1.0410 |
| A4 | 4.00 | 51 | 80 | Evatane 1020 VN3 | 1.0417 | 1.0273 |

TABLE 2b

Fibre dimensions of 3.5 mm loaded fibres processed at an extrusion speed of 3.9 m/min (except variant B3, which was processed at 1.3 m/min)

| variant | Fibre diameter [mm] | Intermediate layer [μm] | Skin [μm] | Skin polymer | R1/R2 | R2/R3 |
|---|---|---|---|---|---|---|
| B1 | 3.49 | 54 | 58 | Evatane 1020 VN3 | 1.0344 | 1.0331 |
| B2 | 3.51 | 52 | 73 | Evatane 1020 VN3 | 1.0434 | 1.0319 |
| B3 | 3.50 | 59 | 261 | Evatane 1040 VN4 | 1.1753 | 1.0413 |
| B4 | 3.50 | 48 | 70 | Evatane 1020 VN3 | 1.0417 | 1.0294 |

The concentration of the active constituents in core and intermediate layer was identical for all rings (10.3% ENG, 0.092% EE in intermediate layer and 0.095% EE in core). The concentration of 0.092 and 0.095% for the intermediate layer and core respectively, was considered (practically) identical.

In-Vitro Release Rates

Results for in-vitro release are shown in Table 3, FIGS. 1 to 4 and FIGS. 6 to 13. FIGS. 1 and 2 show the release rate of etonogestrel from one sample of each kind of ring tested. FIGS. 3 and 4 show the release rate of ethinyl estradiol from one sample of each kind of ring tested. FIGS. 6 to 13 also show release rates of etonogestrel and ethinyl estradiol from one sample of each kind of ring tested (A1-A4 and B1-B4). In Table 3, the release rates are calculated from six (6) samples of each kind of ring tested.

invention was tested at time zero and after 12, 18 and 24 months storage at 30° C./75% R.H. in a closed aluminum foil laminate sachet (WO 99/30976). The burst release of 3 representative NuvaRing® batches was also tested at time zero and after 12, 18 and 24 months storage at 30° C./75% R.H. in said closed aluminum foil laminate sachet. The release rate at time zero was determined by analyzing 12 rings per batch and the release rate after 12, 18 and 24 months was determined by analyzing 6 rings per batch. The results of these analyses are described in Tables 4, 5 and 6. It is apparent that the burst release of all three NuvaRing® batches increases upon storage already after 12 months at 30° C. With exception of variant A3, all seven batches of a ring of the subject invention show a constant or a lower burst release after storage at 30° C. Visual examination of rings from batch A3, revealed that the

TABLE 3

In vitro release rates for all produced batches at t = 0.

| | In-vitro release rate of etonogestrel (μg/day/ring) | | | | In-vitro release rate of EE (μg/day/ring) | | | |
|---|---|---|---|---|---|---|---|---|
| Batch | Day 1 | Average day (2-21) | Rsd (%) | Day 21 | Day 1 | Average day (2-21) | Rsd (%) | Day 21 |
| A1 | 258-264 | 194 | 1 | 177-180 | 22-22 | 14 | 1 | 11-12 |
| A2 | 216-225 | 162 | 1 | 149-152 | 19-20 | 12 | 1 | 10-10 |
| A3 | 179-184 | 119 | 0 | 113-114 | 25-25 | 11 | 0 | 8-9 |
| A4 | 213-221 | 156 | 1 | 130-132 | 19-20 | 12 | 1 | 10-10 |
| B1 | 223-232 | 188 | 1 | 157-163 | 19-21 | 13 | 2 | 10-11 |
| B2 | 191-197 | 158 | 1 | 139-143 | 18-19 | 11 | 1 | 9-10 |
| B3 | 168-172 | 117 | 1 | 110-112 | 26-26 | 10 | 1 | 8-8 |
| B4 | 182-196 | 145 | 2 | 104-111 | 17-19 | 11 | 2 | 9-9 |

The day 1 and day 21 release rate is presented as the range of the individual results of 6 rings (minimum and maximum value are given).
The average day 2-21 release represents the average release rate over the day 2 up to and including day 21. The presented value is the mean of 6 rings.

Assembly

The 4 mm batches (Ax) were cut to pieces of 157 mm and welded with a welding temperature of 130° C. and a welding time of 15 second, on the TWI mono welding unit.

The 3.5 mm fibres were cut into pieces of 157 mm and the ends were glued together (Loctite, type 406 and 770; cat nr. 40621 and 77012).

Thus, a novel three layered ring design, with layers varying from 50 to 300 nm, was processed with limited variations in skin thickness and intermediate layer thickness.

Example 2

Physical Stability

The storage stability of NuvaRing® at normal storage temperature (up to 30° C.) is limited due to the formation of steroid crystals on the surface of the skin of the vaginal ring, which leads to an increased on-set release, the so-called burst release and thus to a decreased physical stability. The burst release (day 1 release) of 8 batches of a ring of the subject increase of the burst release is not due to the formation of steroid crystals on the surface of the ring. The fact that the increase of the burst release of batch A3 is not due to crystal formation on the ring surface is also shown by the small differences observed between individual test result as indicated by the low RSD (relative standard deviation) value.

TABLE 4 day 1 release rate at time zero and after 12 months storage at 30° C./75% R.H.

| | On-Set release | | | |
|---|---|---|---|---|
| NuvaRing ® | Individual results t = 0 | RSD (%) | Individual results t = 12 months | RSD (%) |
| N1 | 186.4, 193.2, 186.6, 185.5, 189.9, 188.5, 187.8, 187.6, 189.6, 184.4, 188.3, 190.2 | 1.3 | 210.6, 191.0, 179.5, 178.6, 171.8, 205.9 | 8.3 |
| N2 | 197.4, 199.0, 199.3, 198.2, 199.7, 198.3, 205.1, 200.5, 200.4, 200.1, 200.3, 198.3 | 1.0 | 188.5, 190.5, 194.4, 195.4, 215.3, 200.1 | 4.9 |

TABLE 4-continued day 1 release rate at time zero and after 12 months storage at 30° C./75% R.H.

On-Set release

| NuvaRing ® | Individual results t = 0 | RSD (%) | Individual results t = 12 months | RSD (%) |
|---|---|---|---|---|
| N3 | 194.6, 197.5, 197.0, 193.8 198.3, 197.5, 198.3, 199.4, 198.7, 204.5, 211.6, 201.8 | 2.4 | 255.1, 325.3, 276.3, 215,0 505.9, 222.5 | 36.6 |
| Ring of the subject invention | | | | |
| A1 | 260.7, 264.9, 263.7, 260.3, 263.6, 261.6, 265.2, 264.7, 263.7, 261.7, 265.5, 258.4 | 0.9 | 210.2, 207.1, 220.7, 217.2, 209.3, 209.2 | 2.5 |
| A2 | 219.5, 221.6, 219.5, 219.2, 219.4, 225.0, 222.5, 221.7, 215.8, 223.6, 218.0, 221.2 | 1.1 | 184.2, 181.1, 176.9, 179.9, 177.3, 177.0 | 1.6 |
| A3 | 181.0, 180.8, 180.0, 182.2, 179.3, 180.7, 180.5, 181.5, 181.2, 182.1, 180.7, 193.6 | 0.6 | 198.7, 194.0, 197.7, 202.5, 199.0, 199.5 | 1.4 |
| A4 | 217.9, 213.4, 216.3, 216.9, 215.1, 219.2, 220.1, 220.6, 221.1, 218.0, 217.9, 219.2, | 1.1 | 169.1, 171.1, 176.6, 176.6, 175.0, 169.3 | 2.0 |
| B1 | 222.9, 230.0, 225.5, 227.8, 230.5, 229.4, 229.5, 226.8, 226.4, 231.9, 232.3, 226.6 | 1.2 | 181.6, 178.4, 180.8, 181.8, 178.1, 179.0 | 0.9 |
| B2 | 194.8, 194.5, 194.3, 197.4, 190.9, 195.2, 194.9, 192.8, 191.5, 192.6, 194.2, 194.0, | 0.9 | 154.1, 152.5, 151.0, 154.3, 154.1, 153.7 | 0.8 |
| B3 | 171.3, 171.3, 170.1, 171.4, 168.8, 172.0, 171.5, 171.5, 169.7, 169.7, 167.5, 167.9 | 0.9 | 179.0, 177.8, 176.6, 183.2, 179.1, 178.9 | 1.2 |
| B4 | 188.2, 189.9, 195.8, 185.9, 189.9, 181.7, 194.3, 192.2, 191.5, 182.5, 189.7, 193.6 | 2.3 | 155.1, 150.6, 148.8, 150.4, 151.6, 148.3 | 1.6 |

TABLE 5 day 1 release rate at time zero and after 18 months storage at 30° C./75% R.H.

On-Set release

| NuvaRing ® | Individual results t = 0 | RSD (%) | Individual results t = 18 months | RSD (%) |
|---|---|---|---|---|
| N1 | 186.4, 193.2, 186.6, 185.5, 189.9, 188.5, 187.8, 187.6, 189.6, 184.4, 188.3, 190.2 | 1.3 | 188.6, 237.0, 301.8, 252.6, 234.0, 186.4 | 18.5 |
| N2 | 197.4, 199.0, 199.3, 198.2, 199.7, 198.3, 205.1, 200.5, 200.4, 200.1, 200.3, 198.3 | 1.0 | 210.8, 183.0, 261.6, 202.1, 241.8, 249.4 | 13.7 |
| N3 | 194.6, 197.5, 197.0, 193.8 198.3, 197.5, 198.3, 199.4, 198.7, 204.5, 211.6, 201.8 | 2.4 | 479.6, 560.2, 510.2, 483.0, 579.4, 477.9 | 8.6 |
| Ring of the subject invention | | | | |
| A1 | 260.7, 264.9, 263.7, 260.3, 263.6, 261.6, 265.2, 264.7, 263.7, 261.7, 265.5, 258.4 | 0.9 | 205.5, 209.1, 201.9, 207.5, 199.0, 198.3 | 2.2 |
| A2 | 219.5, 221.6, 219.5, 219.2, 219.4, 225.0, 222.5, 221.7, 215.8, 223.6, 218.0, 221.2 | 1.1 | 172.5, 174.0, 174.0, 180.5, 177.0, 174.5 | 1.7 |
| A3 | 181.0, 180.8, 180.0, 182.2, 179.3, 180.7, 180.5, 181.5, 181.2, 182.1, 180.7, 193.6 | 0.6 | 194.0, 203.4, 197.7, 201.5, 190.2, 197.9 | 2.5 |
| A4 | 217.9, 213.4, 216.3, 216.9, 215.1, 219.2, 220.1, 220.6, 221.1, 218.0, 217.9, 219.2, | 1.1 | 166.9, 163.2, 165.7, 168.1, 159.4, 166.4 | 1.9 |

TABLE 5-continued day 1 release rate at time zero and after 18 months storage at 30° C./75% R.H.

On-Set release

| NuvaRing ® | Individual results t = 0 | RSD (%) | Individual results t = 18 months | RSD (%) |
|---|---|---|---|---|
| B1 | 222.9, 230.0, 225.5, 227.8, 230.5, 229.4, 229.5, 226.8, 226.4, 231.9, 232.3, 226.6 | 1.2 | 171.8, 169.7, 167.6, 173.7, 171.6, 169.4 | 1.3 |
| B2 | 194.8, 194.5, 194.3, 197.4, 190.9, 195.2, 194.9, 192.8, 191.5, 192.6, 194.2, 194.0, | 0.9 | 147.6, 146.1, 146.0, 146.8, 142.9, 143.7 | 1.3 |
| B3 | 171.3, 171.3, 170.1, 171.4, 168.8, 172.0, 171.5, 171.5, 169.7, 169.7, 167.5, 167.9 | 0.9 | 172.3, 170.9, 171.7, 172.0, 169.5, 177.1 | 1.5 |
| B4 | 188.2, 189.9, 195.8, 185.9, 189.9, 181.7, 194.3, 192.2, 191.5, 182.5, 189.7, 193.6 | 2.3 | 147.5, 146.5, 142.4, 127.3, 145.6, 145.5 | 5.4 |

TABLE 6 day 1 release rate at time zero and after 24 months storage at 30° C./75% R.H.

On-Set release

| NuvaRing ® | Individual results t = 0 | RSD (%) | Individual results t = 24 months | RSD (%) |
|---|---|---|---|---|
| N1 | 186.4, 193.2, 186.6, 185.5, 189.9, 188.5, 187.8, 187.6, 189.6, 184.4, 188.3, 190.2 | 1.3 | 199.0, 175.9, 219.9, 188.9, 206.9, 184.8 | 8.2 |
| N2 | 197.4, 199.0, 199.3, 198.2, 199.7, 198.3, 205.1, 200.5, 200.4, 200.1, 200.3, 198.3 | 1.0 | 247.0, 275.7, 297.3, 371.9, 215,6, 269.0 | 19.0 |
| N3 | 194.6, 197.5, 197.0, 193.8 198.3, 197.5, 198.3, 199.4, 198.7, 204.5, 211.6, 201.8 | 2.4 | 271.3, 262.2, 268.1, 247.2, 436.6, 329.4 | 23.6 |
| Ring of the subject invention | | | | |
| A1 | 260.7, 264.9, 263.7, 260.3, 263.6, 261.6, 265.2, 264.7, 263.7, 261.7, 265.5, 258.4 | 0.9 | 206.4, 208.6, 201.8, 203.7, 209.9, 213.7 | 2.1 |
| A2 | 219.5, 221.6, 219.5, 219.2, 219.4, 225.0, 222.5, 221.7, 215.8, 223.6, 218.0, 221.2 | 1.1 | 179.1, 172.1, 173.4, 179.8, 179.8, 172.8 | 2.0 |
| A3 | 181.0, 180.8, 180.0, 182.2, 179.3, 180.7, 180.5, 181.5, 181.2, 182.1, 180.7, 193.6 | 0.6 | 197.7, 195.8, 196.8, 197.8, 197.7, 204.9 | 1.6 |
| A4 | 217.9, 213.4, 216.3, 216.9, 215.1, 219.2, 220.1, 220.6, 221.1, 218.0, 217.9, 219.2, | 1.1 | 170.1, 163.6, 163.5, 168.2, 164.6, 166.9 | 1.6 |
| B1 | 222.9, 230.0, 225.5, 227.8, 230.5, 229.4, 229.5, 226.8, 226.4, 231.9, 232.3, 226.6 | 1.2 | 171.3, 170.3, 172.1, 175.9, 168.2, 171.8 | 1.5 |
| B2 | 194.8, 194.5, 194.3, 197.4, 190.9, 195.2, 194.9, 192.8, 191.5, 192.6, 194.2, 194.0, | 0.9 | 143.5, 145.8, 146.8, 148.0, 150.0, 148.8 | 1.6 |
| B3 | 171.3, 171.3, 170.1, 171.4, 168.8, 172.0, 171.5, 171.5, 169.7, 169.7, 167.5, 167.9 | 0.9 | 173.9, 173.0, 173.9, 177.4, 175.4, 175.9 | 0.9 |
| B4 | 188.2, 189.9, 195.8, 185.9, 189.9, 181.7, 194.3, 192.2, 191.5, 182.5, 189.7, 193.6 | 2.3 | 145.0, 145.6, 144.9, 143.9, 142.6, 143.4 | 0.8 |

Example 3

Improved Three-Layered Ring Versus Ring Described in U.S. Pat. No. 4,292,965

This example illustrates the benefits of the subject improved three-layered ring relative to the three-layered ring described in U.S. Pat. No. 4,292,965.

In U.S. Pat. No. 4,292,965 two steroids are accommodated in the intermediate layer; no steroid is present in the core.

The essence of the improved three-layer ring is that the release rate of two or more steroids can be adjusted independently from one another and that the ring is able to sustain this release rate for a more prolonged period of time while maintaining physical stability at room temperature conditions. This example demonstrates the advantage of the improved three-layered ring which also has a loaded core over a ring design with a non-medicated core as described in U.S. Pat. No. 4,292,965.

It is not possible to load more than one steroid in the intermediate layer in the crystalline form and have independent release. In order to adjust the release rate of two (or more) steroids from one compartment, only one steroid can be present in the crystalline phase and the other(s) has to be present in the dissolved phase. In case steroid A is partly present in the crystalline phase, the steroid in the crystalline lattice will be in dynamic equilibrium with dissolved steroid. Since the concentration of steroid A is pre-determined, the release rate of steroid A can be adjusted by choosing the right skin thickness. Considering the fact that the skin thickness is already used as a means to adjust the release rate of steroid A, the release rate of the second component, steroid B can only be tuned by choosing the appropriate concentration. Since steroid B is only present in the dissolved form, more steroid can be incorporated into the ring (while maintaining the same concentration gradient over the membrane) by increasing the volume of the reservoir (the core). Thus, the volume of the reservoir determines the amount of dissolved steroid B that can be loaded in the ring.

For ring A2 of the subject invention (see example 1) the volume of the intermediate layer and core reservoir can be calculated as follows. The fibre dimensions of ring A2 are approximately; length 15.7 cm, diameter 4.0 mm, thickness intermediate layer about 60 μm and skin about 80 μm and the volume of the intermediate layer and the core of approximately $V_{int}=0.11$ ml and $V_{core}=1.71$ ml. The densities of both core and intermediate layer are relatively close to 1 g/ml and consequently the mass of the core and intermediate layer are approximately 1.71 g and 0.11 g respectively. The concentration EE in the core and intermediate layer is approximately 0.095% m/m. and hence the core contains approximately 1620 μg EE and the intermediate layer contains approximately 106 μg of EE. Thus, in this particular case (A2) more than approximately 15 times more EE can be loaded in the improved three-layered design compared to a ring with a non-medicated core.

The release of EE from ring A2 as function of time is presented in FIG. 3 and can be used to illustrate the advantage of loading the core with EE. The semi-steady state release (release day 2-21) is between 15 and 10 μg/day and the content of the intermediate layer alone (106 μg) would be insufficient to sustain a fairly constant release rate over a period longer than a few days. After less then 7 days the intermediate layer would be almost completely depleted and the release rate would drop already dramatically after a few days.

Moreover, in a ring design such as that of U.S. Pat. No. 4,292,965, due to internal diffusion into the core, a non-equilibrium situation is obtained and consequently the concentration EE in the intermediate layer will decrease, which results in a pharmaceutical product with an unstable release profile. However, when the core is loaded with the same concentration EE as in the intermediate layer the desired equilibrium situation is obtained.

This non-steady state behaviour due to internal diffusion (also called back diffusion) is inherent to the three-layer design according to U.S. Pat. No. 4,292,965 while the improved three layer design eliminates also these undesired effects.

Example 4

Preparation of Additional Three-Layered Rings

Twenty (20) additional three-layer fibres were prepared (E-X). The fibre variants had a dimension of 4 mm (E-V), 3 mm (variant W) and 5 mm (variant X). All fibres were spun from a single capillary (3.6 mm).

Several core and intermediate granulates (C1-C4 and D1-D2 respectively) were prepared using essentially the same method as described in Example 1 with the following minor changes:

Granulates C4, D1 and D2 were mixed in a stainless steel drum using a Rhönrad (Barrel-hoop principle) with a fixed speed of approximately of 47 rpm for 60 minutes.

TABLE 7

Composition core granulates

| Variant | Etonogestrel | Ethinyl estradiol | Ateva 2820A | Magnesium stearate | Total |
| --- | --- | --- | --- | --- | --- |
| C1 | — | 0.16% | 99.7% | 0.1% | 100.0% |
| C2 | — | 0.13% | 99.8% | 0.1% | 100.0% |
| C3 | — | 0.20% | 99.7% | 0.1% | 100.0% |
| C4 | 0.33% | 0.16% | 99.4% | 0.1% | 100.0% |

TABLE 8

Composition intermediate layer granulates

| Variant | Etonogestrel | Ethinyl estradiol | Ateva 2820A | Magnesium stearate | Total |
| --- | --- | --- | --- | --- | --- |
| D1 | 10.5% | 0.16% | 89.2% | 0.1% | 100.0% |
| D2 | 52.5% | 0.16% | 47.2% | 0.1% | 100.0% |

Tri-Layer Co-Extrusion

A Fournétrico-extruder (25/18/18 mm) was used for the production of the three-layered fibres. The 25 mm extruder processed the core layer, whereas the two 18 mm extruders processed the intermediate layer and the skin (outer layer) respectively. The three extruders were connected with a 3-compartment spinning block with 3 separate spinning pumps (to control the volume flow rate (melt flow) of each layer). The three melt flows were combined in a spinneret resulting in a fibre with 3 layers. A capillary of 3.6 mm was used. All fibres were extruded at an extrusion temperature of 110° C.

The spinning rate was adjusted to obtain the desired fibre diameter of 3, 4 or 5 mm. The desired layer thickness for skin and intermediate layer was obtained by adjustment of the spinning pumps. Each of the tri-layer fibre variants was produced by using the appropriate spinning rate and spinning pump settings (totally 20 variants, E-X). After approximately 20 minutes tri-layer co-extrusion of each variant, the tri-layer fibre was collected on a stainless steel reel for 120 minutes. The outer diameter of the fibre was measured on-line continuously using a laser micrometer and recorded. At the start and at the end of these 120 minutes, the diameter of the fibre, thickness of the middle layer, and the thickness of the skin was measured and recorded. The variants W and X were collected for only 30 minutes. The loaded fibres were processed at an extrusion speed of 2.00 m/min for variants E-V, at 3.59 m/min for variant W, and at 1.28 m/min for variant X.

Fibre Dimensions

The intermediate layer thickness and skin thickness were determined for each fibre variant from fibre pieces of 4 samples during the trico-extrusion. The outer diameter was determined for each fibre variant from fibre pieces of 6 samples during processing on trico-extruded fibres. The outer diameter was determined by means of a laser thickness gauge (Zumbach). The intermediate layer and skin thickness were determined using a microscope (Jena). The results for the loaded batches are shown in Tables 9a, 9b and 9c.

TABLE 9a

Fibre dimensions of 4 mm loaded fibres processed at an extrusion speed of 2.00 m/min

| Variant | Fibre diameter [mm] | Composition core | Intermediate layer [μm] | Composition intermediate layer | Skin [μm] | R1/R2 | R2/R3 | Skin polymer |
|---|---|---|---|---|---|---|---|---|
| E | 4.01 | C1 | 61 | D1 | 110 | 1.0580 | 1.0333 | Ateva 1070 |
| F | 4.01 | C3 | 60 | D1 | 100 | 1.0525 | 1.0325 | Ateva 1070 |
| G | 4.02 | C3 | 63 | D1 | 126 | 1.0669 | 1.0346 | Ateva 1070 |
| H | 4.02 | C2 | 53 | D1 | 94 | 1.0491 | 1.0284 | Ateva 1070 |
| I | 4.04 | C2 | 62 | D1 | 123 | 1.0648 | 1.0338 | Ateva 1070 |
| J | 4.02 | C1 | 148 | D1 | 110 | 1.0579 | 1.0845 | Ateva 1070 |
| K | 4.00 | C1 | 28 | D2 | 111 | 1.0588 | 1.0150 | Ateva 1070 |
| L | 4.03 | C4 | 67 | D1 | 112 | 1.0589 | 1.0365 | Ateva 1070 |
| M | 4.01 | C1 | 61 | D1 | 146 | 1.0780 | 1.0339 | Ateva 1231 |
| N | 4.03 | C2 | 60 | D1 | 133 | 1.0701 | 1.0329 | Ateva 1231 |
| O | 4.01 | C2 | 63 | D1 | 167 | 1.0909 | 1.0355 | Ateva 1231 |
| P | 4.02 | C3 | 63 | D1 | 132 | 1.0703 | 1.0347 | Ateva 1231 |
| Q | 4.02 | C3 | 60 | D1 | 161 | 1.0871 | 1.0335 | Ateva 1231 |
| R | 4.04 | C1 | 70 | D1 | 315 | 1.1848 | 1.0428 | Ateva 1525 |
| S | 4.05 | C2 | 69 | D1 | 277 | 1.1585 | 1.0411 | Ateva 1525 |
| T | 4.02 | C2 | 68 | D1 | 335 | 1.2000 | 1.0423 | Ateva 1525 |
| U | 4.04 | C3 | 67 | D1 | 298 | 1.1731 | 1.0405 | Ateva 1525 |
| V | 4.04 | C3 | 65 | D1 | 334 | 1.1981 | 1.0401 | Ateva 1525 |

TABLE 9b

Fibre dimensions of 3 mm loaded fibres processed at an extrusion speed of 3.59 m/min

| Variant | Fibre diameter [mm] | Composition core | Intermediate layer [μm] | Composition intermediate layer | Skin [μm] | R1/R2 | R2/R3 | Skin polymer |
|---|---|---|---|---|---|---|---|---|
| W | 3.03 | C1 | 45 | D1 | 83 | 1.0580 | 1.0324 | Ateva 1070 |

TABLE 9c

Fibre dimensions of 5 mm loaded fibres processed at an extrusion speed of 1.28 m/min

| Variant | Fibre diameter [mm] | Composition core | Intermediate layer [μm] | Composition intermediate layer | Skin [μm] | R1/R2 | R2/R3 | Skin polymer |
|---|---|---|---|---|---|---|---|---|
| X | 5.00 | C1 | 74 | D1 | 138 | 1.0584 | 1.0323 | Ateva 1070 |

In-Vitro Release Rates

Results for in-vitro release are shown in Table 10 and FIGS. 14 to 21 which show release rates of etonogestrel and ethinyl estradiol of all fibres (E-W). In Table 10 and also in FIGS. 14-21, the release rates are calculated from six (6) samples of each kind of ring tested.

TABLE 10

In vitro release rates for all produced batches at t = 0

| Batch | In-vitro release rate of etonogestrel (μg/day/ring) | | | | In-vitro release rate of EE (μg/day/ring) | | | |
|---|---|---|---|---|---|---|---|---|
| | Day 1 | Average day (2-21) | Rsd (%) | Day 21 | Day 1 | Average day (2-21) | Rsd (%) | Day 21 |
| E | 140-153 | 94 | 1 | 89-90 | 23-24 | 14 | 3 | 12-13 |
| F | 153-162 | 108 | 2 | 99-104 | 29-30 | 19 | 2 | 17-18 |
| G | 125-131 | 82 | 1 | 76-79 | 24-25 | 15 | 2 | 12-14 |
| H | 148-157 | 106 | 2 | 97-101 | 20-21 | 13 | 3 | 10-12 |
| I | 122-127 | 82 | 1 | 76-79 | 17-18 | 10 | 4 | 8-9 |
| J | 208-214 | 101 | 1 | 91-93 | 23-24 | 14 | 2 | 12-13 |
| K | 123-135 | 95 | 2 | 88-93 | 21-23 | 13 | 3 | 11-12 |
| L | 178-187 | 98 | 2 | 87-91 | 21-23 | 13 | 3 | 11-11 |
| M | 187-197 | 123 | 1 | 113-117 | 34-35 | 19 | 2 | 16-17 |
| N | 193-198 | 133 | 1 | 121-125 | 30-31 | 17 | 2 | 14-15 |
| O | 165-171 | 106 | 1 | 98-101 | 26-28 | 14 | 2 | 11-12 |
| P | 182-208 | 138 | 1 | 127-131 | 39-44 | 25 | 2 | 22-23 |
| Q | 170-180 | 112 | 1 | 103-107 | 38-40 | 21 | 2 | 19-19 |
| R | 186-203 | 118 | 1 | 109-113 | 26-29 | 19 | 2 | 15-17 |
| S | 226-236 | 131 | 1 | 123-126 | 36-38 | 18 | 2 | 14-15 |
| T | 190-197 | 110 | 1 | 102-105 | 27-29 | 15 | 2 | 12-12 |
| U | 218-224 | 125 | 1 | 116-119 | 41-44 | 24 | 2 | 20-22 |
| V | 181-193 | 111 | 1 | 103-107 | 30-32 | 22 | 2 | 19-19 |
| W | 120-122 | 96 | 1 | 83-85 | 21-21 | 13 | 2 | 11-12 |
| X | 134-144 | 84 | 3 | 77-84 | 21-22 | 12 | 3 | 10-12 |

The day 1 and day 21 release rate is presented as the range of the individual results of 6 rings (minimum and maximum value are given)
The average day 2-21 release represents the average release rate over the day 2 up to and including day 21. The presented value is the mean of 6 rings.

Assembly

The 4 mm fibres (E-V) were cut to pieces of 157 mm and welded with a welding temperature of 130° C. and a welding time of 17 seconds, on a CCM (Centrum voor Constructie en Mechatronica, The Netherlands) assembly unit. Fibres W and X were manually cut to 157 mm and the fibre ends were glued together using Loctite adhesive (type 406 and 770; cat nr. 40621 and 77012).

The invention claimed is:

1. A vaginal ring comprising (i) a drug-loaded ethylene-vinylacetate copolymer core, (ii) a drug-loaded ethylene-vinylacetate copolymer intermediate layer and (iii) a non-medicated ethylene-vinylacetate copolymer skin covering the intermediate layer, wherein said intermediate layer is loaded with (a) crystals of a first pharmaceutically active compound, wherein the first pharmaceutically active compound is a steroid and with (b) a second pharmaceutically active compound in dissolved form and wherein said core is loaded with the second pharmaceutically active compound such that the pharmaceutically active compound in the core is present only in dissolved form and wherein the second pharmaceutically active compound is etonogestrel.

2. The vaginal ring according to claim 1 which is physically stable at about 18-30° C.

3. The vaginal ring according to claim 1 wherein etonogestrel in the core is present in the same concentration as in the intermediate layer.

4. The vaginal ring according to claim 3 wherein etonogestrel is present in the intermediate layer at about 6-80% by weight.

5. A method of contraception which comprises the steps of (i) positioning the vaginal ring of claim 1 within the female vaginal tract and (ii) retaining the system within the vaginal tract for at least about 21 days.

6. The vaginal ring according to claim 1, wherein the core and the intermediate layer comprise a different grade of ethylene-vinylacetate copolymer.

* * * * *